United States Patent
Pendergast et al.

(10) Patent No.: US 6,255,074 B1
(45) Date of Patent: *Jul. 3, 2001

(54) ABL-INTERACTOR PROTEIN

(75) Inventors: Ann-Marie Pendergast, Durham, NC (US); Zonghan Dai, Englewood, CO (US)

(73) Assignee: Duke University, Durham, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 09/051,982

(22) PCT Filed: Oct. 25, 1996

(86) PCT No.: PCT/US96/17047
    § 371 Date: Jul. 8, 1998
    § 102(e) Date: Jul. 8, 1998

(87) PCT Pub. No.: WO97/15587
    PCT Pub. Date: May 1, 1997

Related U.S. Application Data

(63) Continuation-in-part of application No. 08/549,004, filed on Oct. 27, 1995, now Pat. No. 5,969,101.

(51) Int. Cl.[7] .......................... C12P 21/00; C07H 21/04; C07K 14/46; C12N 1/21; C12N 5/10

(52) U.S. Cl. .................... 435/69.1; 435/32.5; 435/252.3; 530/350; 530/326; 530/324; 536/23.5

(58) Field of Search .................................. 435/69.1, 325, 435/252.3; 530/350, 326, 324; 536/23.5

(56) References Cited

PUBLICATIONS

Dai et al, "Oncogene Abl and Src tyrosine kinases elicit the ubiquitin–dependent degradation of target proteins through a Ras–independent pathway", Genes & Development 12:1415–1424 (1998).
Taki et al, "Abl–1, a Human Homology to Mouse Abl–Interactor 1. Fuses the MLL Gene in Acute Myeloid Leukemia With t(10;11)(p11.2;q23)", Blood 92(4):1125–1130 (1998).
Cicchetti et al, "Identification of a Protein That Binds to the SH3 Region of Abl and Is Similar to Bcr and GAP–rho", Science 257:803–806 (1992).
Reddy et al, "The cloning and characterization of a localized maternal transcript in Xenopus laevis whose zygotic counterpart is detected in the CNS", Mechanisms Development 39(3):143–150 (1992).
Schulz et al, Principles of Protein Structure 314:14–16 (1979), Publisher: (Springer–Verlag, New York, N.Y.).
Ren, PIR–International Protein Sequence Database Accession No. G01936, National Biomedical Research Foundation, Washington, DC 20007, Dec. 21, 1996.
Lowenstein et al, "The SH2 and SH3 Domain–Containing Protein GRB2 Links Receptor Tyrosine Kinases to ras Signaling", Cell 70:431–442 (1992).
Cicchetti et al, "3BP–1, an SH3 domain binding protein, has GAP activity for Rac and inhibits growth factor–induced membrane ruffling in fibroblasts", The EMBO Journal 14(13):3127–3135 (1995).
Dai et al, "Abi–2, a novel SH3–containing protein interacts with the c–Abl tyrosine kinase and modulates c–Abl transforming activity", Genes & Development 9:2569–2582 (1995).
Shi et al, "Abl–interactor–1, a novel SH3 protein binding to the carboxy–terminal portion of the Abl protein, suppresses v–abl transforming activity", Genes & Development 9:2583–2597 (1995).
Dai et al, "Cloning and Characterization of a cABL Interacting Protein", Abstract/Tenth Annual Meeting on Oncogenes, p. 338, Jun. 21–25, 1994. Hood College, Frederick, Maryland.
Feller et al, "SH2 and SH3 domains as molecular adhesives: the interactions of Crk and Abl", TIBS 19, Nov. 1994.
Taniuchi et al, "Antigen–receptor induced clonal expansion and deletion of lymphocytes are imparied in mice lacking HS1 protein, a substrate of the antigen–receptor–coupled tyrosine kinases", The EMBO Journal 14(15):3664–3678 (1995).
Fukuda et al, "Restoration of surface lgM–mediated apoptosis in an anti–lgM–resistant variant of WEHI–231 lymphoma cells by HS1, a protein–tyrosine kinase substrate", Proc. Natl. Acad. Sci. USA 92:7302–7306 (1995).
Zappavigna et al, "Specificity of HOX protein function depends on DNA–protein and protein–protein interactions, both mediated by the homeo domain", Genes & Development 8:732–744 (1994).
Kharbanda et al, "Activation of the c–Abl tyrosine kinase in the stress response to DNA–damaging agents", Nature 376:785–788 (1995).
Wong et al. Identification of ArgBP1, an Arg protein tyrosine kinase binding protein that is the human homologue of a CNS–specific Xenopus gene. Oncogene, (May 2, 1996) 12 (9) 1921–9.*
Lodish et al. Molecular Cell Biology, 3rd edition, Mar. 1995, W. H. Freeman & Co., p. 266.*
Bowie et al. Deciphering the message in protein sequences: tolerance to amino acid substitutions. Science, (Mar. 16, 1990) 247 (4948) 1306–10.*
Ren, R. GenBank database record, National Center for Biotechnology Information, Bethesda, Maryland, USA. Accession No. U31089. Sep. 16, 1995.*
Sambrook et al. Molecular Cloning: A Laboratory Manual Second Edition vol. 1, 2 and 3. Cold Spring Harbor Laboratory Press: Cold Spring Harbor, New York, U.S.A. Nov., 1989, pp. 16.2, 17.2–17.4, Sep. 1995.*
Cicchetti et al. 3BP–1, an SH3 domain binding protein, has GAP activity for Rac and inhibits growth factor–induced membrane ruffling in fibroblasts. Embo Journal. Jul. 3, 1995, vol. 14, pp. 3127–3135, see entire document.

* cited by examiner

Primary Examiner—David Romeo
(74) Attorney, Agent, or Firm—Nixon & Vanderhye P.C.

(57) ABSTRACT

The present invention relates to a protein that interacts with the cAb1 protein tyrosine kinase and to a nucleic acid sequence encoding same. The invention also relates to complexes of the protein of the invention and cAb1 and to the use of such complexes in the identification of therapeutic and diagnostic agents.

21 Claims, 18 Drawing Sheets

Fig. 1A

```
1   MSCRCWISRHPSYEGWNLQSIIFHKQIRGVDLESTFVTKFGNNCSLRLNETVDIHKEKVA   60
61  RREIGILTTNKNTSRTHKIIAPANLERPVRYIRKPIDYTILDDIGHGVKVSTQNMKMGGL  120
121 PRTTPPTQKPPSPPMSGKGTLGRHSPYRTLEPVRPPVVPNDYVPSPTRNMAPSQQSPVRT  180
181 ASVNQRNRTYSSSGSSGGSHPSSRSSSRENSGSGSVGVPIAVPTPSPPSVFPGHPVQFYS  240
241 MNRPASRHTPPTIGGSLPYRRPPSITSQTSLQNQMNGGPFYSQNPVSDTPPPPPPVEEPV  300
301 FDESPPPPPPPEDYEEEEAAVVEYSDPYAEEDPPWAPRSYLEKVVAIYDYTKDKEDELSF  360
361 QEGAIIYVIKKNDDGWYEGVMNGVTGLFPGNYVESIMHYSE   401
```

Fig. 1B

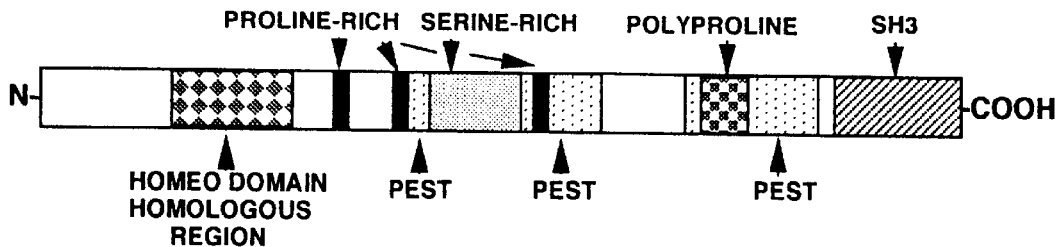

Fig. 1C

```
    ftz  KR.TRQTYTRYQTLELEKEFHFNRYITRRRRIDIANALSLSERQIKIWFQNRRM
    hxa3 KR.GRTAYTRPQLVELEKEFHFNRYLMRPRRVEMANLLNLTERQIKIWFQNRRM
    hxa4 KR.SRTAYTRQQVLELEKEFHFNRYLTRRRRIEIAHTLCLSERQVKIWFQNRRM
    hxd3 KR.VRTAYTSAQLVELEKEFHFNRYLCRPRRVEMANLLNLTERQIKIWFQNRRM
    hxd4 KR.SRTAYTRQQVLELEKEFHFNRYLTRRRRIEIAHTLCLSERQIKIWFQNRRM
  hxli39 KR.QRTAYTRNQVLELEKEFHTHKYLTRKRRIEVAHSLMLTERQVKIWFQNRRM
     zen KR.SRTAFSSLQLIELEREFHLNKYLARTRRIEISQRLALTERQVKIWFQNRRM
   abi-2 KNTSRTHKIIAPAN.LERPV...RYI.R.KPIDYT.ILDDIGHGVKVSTQNMKM
    cons. K  RT     LEK F   RYL R R IE     L   R IKIWFQN RM
                        R         I   K VD         H V V    K
```

Fig. 2

```
                                                                        ┌─START
   1  cccaatcctt  agcaagtgtt  gcctatctga  taaacacctt  ggccaacaat  gtcctgcaga
  61  tgctggatat  ccaggcatcc  cagctacgaa  ggatggaatc  ttcaatcaat  catatttcac
 121  aagcaaatta  gaggcgttga  tcttgagtcg  acttttgtga  ccaaatttgg  aaacaattgc
 181  agtttgagat  tgaatgagac  agttgatatt  cataaagaga  aagttgcaag  aagagaaatt
 241  ggtatttttga  ctaccaataa  aaacacttca  aggacacata  agattattgc  tccagccaac
 301  cttgaacgac  cagttcgtta  tattagaaaa  cctattgact  atacaattct  agatgatatt
 361  ggacatggag  taaaggtgag  taccccagaaac  atgaagatgg  gtgggctgcc  gcgtacaaca
 421  cctccaactc  agaagccccc  tagtccccct  atgtcaggga  aaggacact  tgggcggcac
 481  tcccctatc  gcacactgga  gccagtgcgt  cctccagtgg  taccaaatga  ttacgtacct
 541  agccaaccc  gtaatatgc  tccctcgcag  cagagcccctg  tgaggacagc  ttctgtgaat
 601  caaagaaatc  gaacttacag  cagcagtggg  agtagtggag  ggagccaccc  aagtagtcgg
 661  agcagcagtc  gagagaacag  tggaagtggt  agtgtggggg  ttcctattgc  tgttcctact
 721  ccatctcctc  ccagtgtctt  tccagttcat  cctgtacagt  tctacagcat  gaatagccct
 781  gcctctcgcc  atactccccc  aacaataggg  ggctcgttgc  cctatagacg  ccctccttcc
 841  attacttcac  aaacaagcct  tcagaatcag  atgaatggag  gacctttta  tagccagaat
 901  ccagtttcag  atacaccacc  tccaccgcca  cctgtggaag  aaccagtctt  tgatgagtct
 961  cccccacctc  ctcctcctcc  agaagattac  gaagaggagg  aagctgctgt  ggttgagtat
1021  agtgatcctt  atgctgaaga  ggacccaccg  tgggctccac  gttcttactt  ggaaaaggtt
1081  gtgcaattt  atgactatac  aaaagacaag  gaagatgagc  tgtccttcca  ggaaggagcc
1141  attatttatg  tcatcaagaa  gaatgacgat  ggttggtatg  agggagttat  gaatggagtg
1201  actggctttt  ttcctgggaa  ttacgttgag  tctatcatgc  attattctga  gtaaagctca
1261  gcaggctgt  gcttgcctca  caggaatagt  caggtcttcc  cagattatct  gaaggccctg
1321  gggattccac  tccagtaaag  tagaatgaag  gatacaaatg  ataaaaatta  cactttttt
1381  tttgtttat  tcccccagtat  taaaaacaaa  gcaagctgag  tctgaacaaa
                              └─POLY A                               └─STOP
                                SITE
┌─POTENTIAL
  SPLICE
  SITE
```

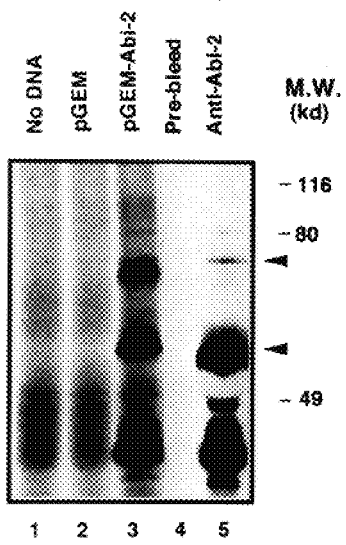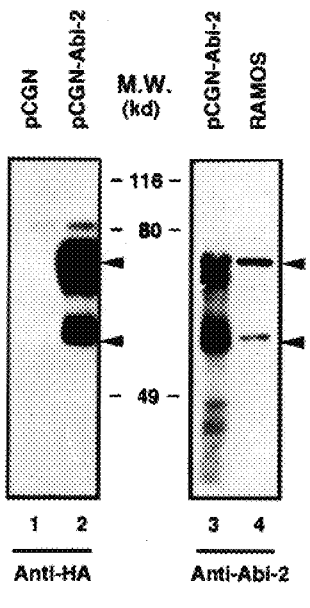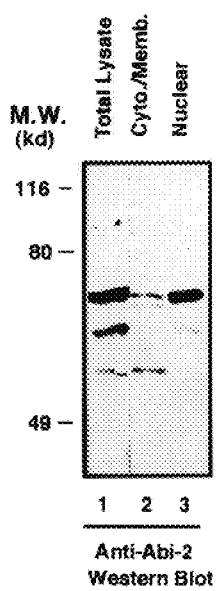
Fig. 3A In Vitro Translation
Fig. 3B In Vivo Expression
Fig. 3C Subcellular Localization

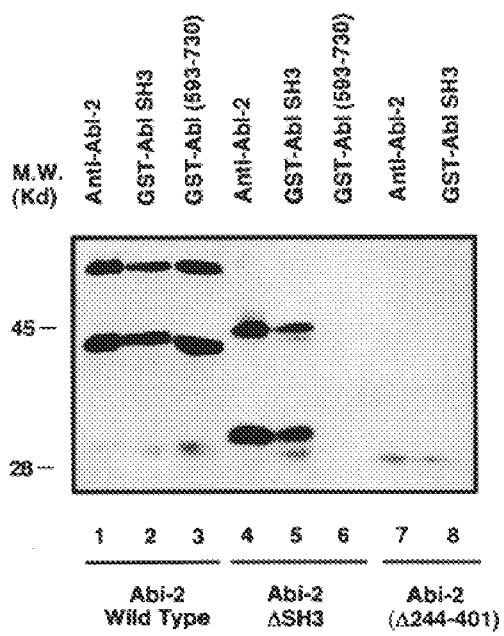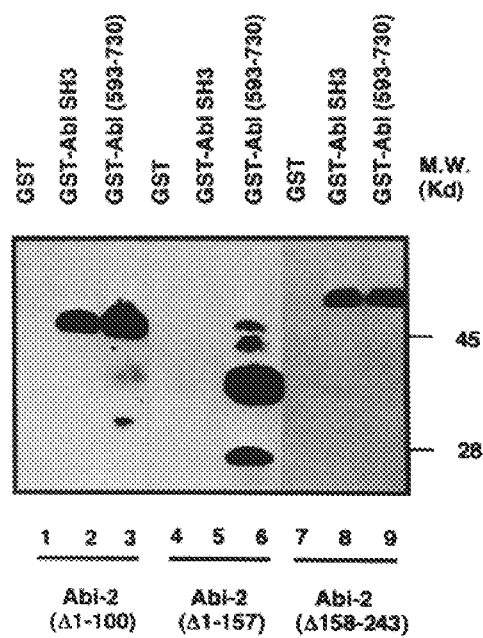

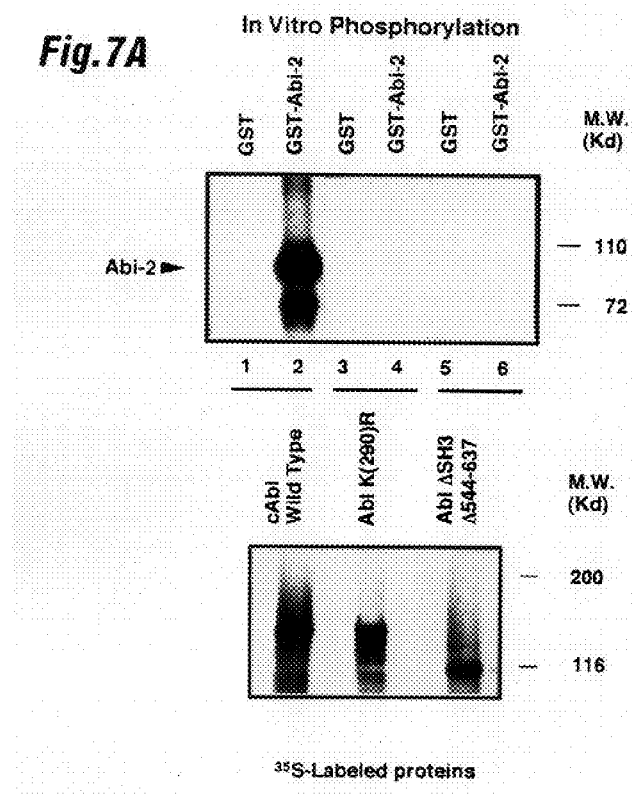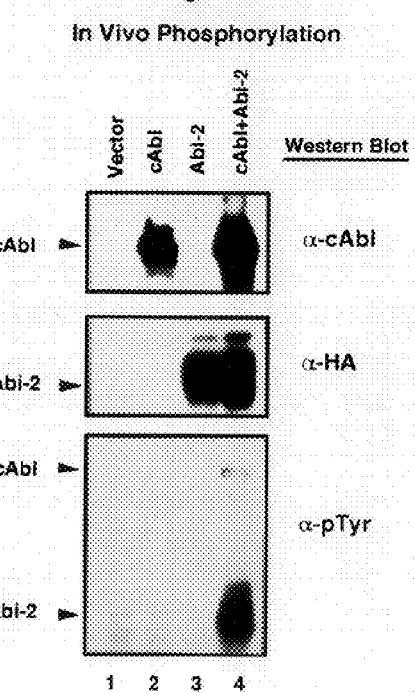

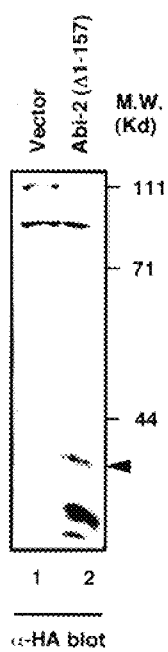
Fig.8A
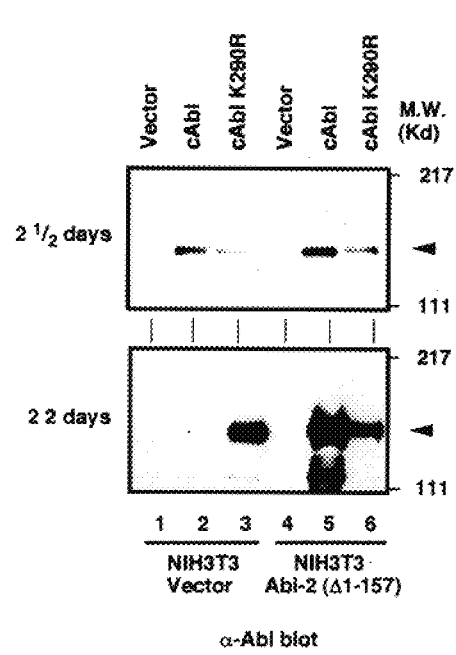
Fig.8B
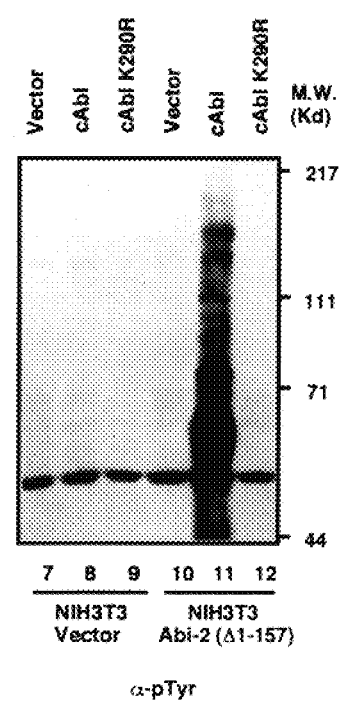

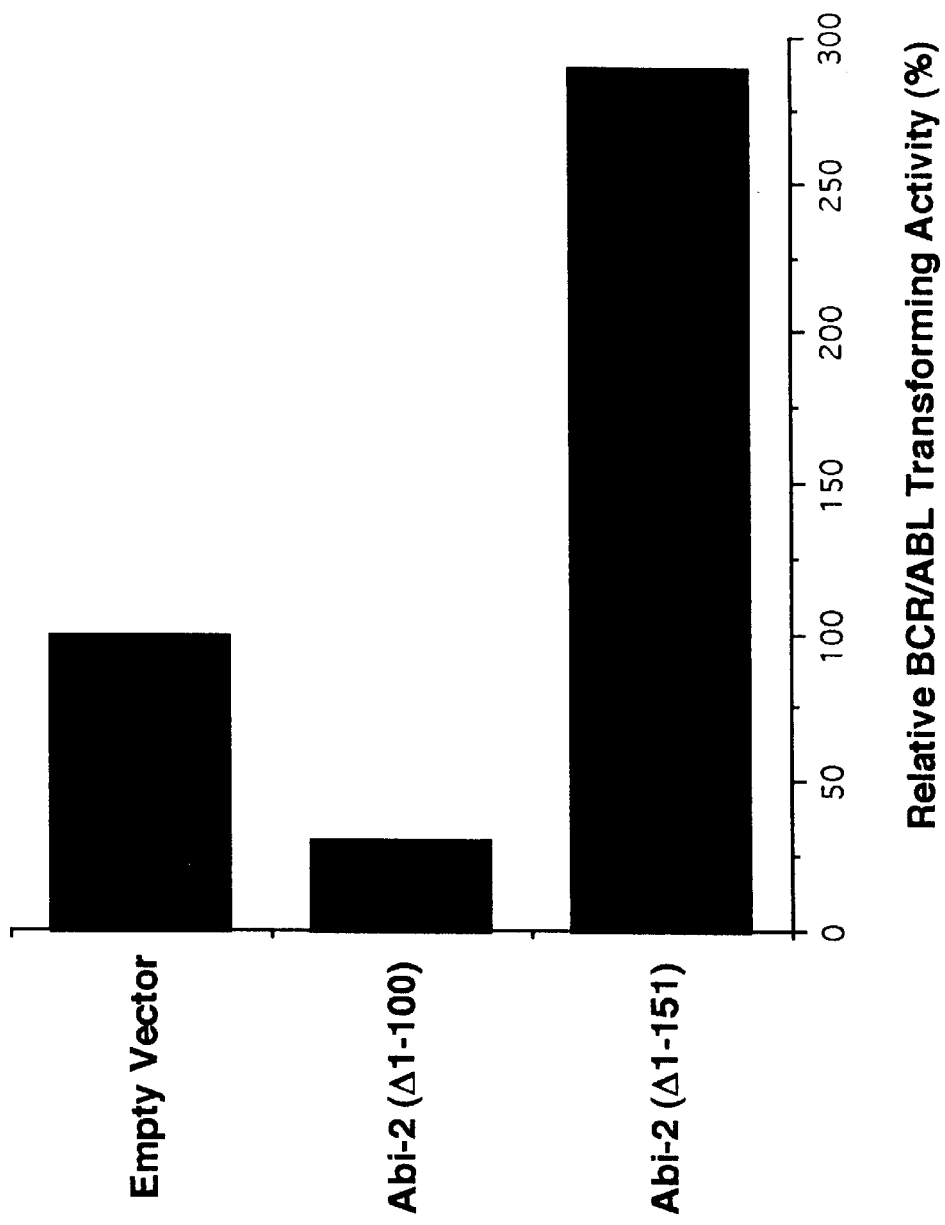

Correlation of Human Sequences Detected by Abi-2 cDNA with Human Chromosomes in Rodent X Human Somatic Cell Hybrids

| Hybridization/ Chromosome | | Human chromosomes | | | | | | | | | | | | | | | | | | | | | | |
|---|---|---|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | X | Y |
| Concordant | +/+ | 3 | 6 | 4 | 3 | 4 | 5 | 4 | 5 | 0 | 2 | 1 | 3 | 3 | 5 | 6 | 1 | 6 | 5 | 4 | 5 | 3 | 3 | 0 | 1 |
| | −/− | 11 | 12 | 6 | 5 | 7 | 5 | 5 | 5 | 11 | 6 | 8 | 5 | 9 | 5 | 6 | 11 | 3 | 9 | 7 | 6 | 7 | 8 | 10 | 9 |
| Discordant | +/− | 3 | 0 | 2 | 2 | 1 | 1 | 1 | 0 | 6 | 3 | 3 | 2 | 1 | 0 | 0 | 4 | 0 | 1 | 2 | 1 | 2 | 1 | 4 | 4 |
| | −/+ | 1 | 0 | 5 | 6 | 5 | 7 | 6 | 5 | 1 | 2 | 4 | 7 | 2 | 7 | 3 | 1 | 9 | 3 | 2 | 5 | 5 | 4 | 1 | 2 |
| Discordant clones | | 4 | 0 | 7 | 8 | 6 | 8 | 7 | 5 | 7 | 5 | 7 | 9 | 3 | 7 | 3 | 5 | 9 | 4 | 4 | 6 | 7 | 5 | 5 | 6 |
| Informative clones* | | 18 | 18 | 17 | 16 | 17 | 18 | 16 | 15 | 18 | 13 | 16 | 17 | 15 | 17 | 15 | 17 | 18 | 18 | 15 | 17 | 17 | 16 | 15 | 16 |

*Data for chromosomes involved in rearrangement of present at a frequency of 0.1 or less were excluded.

ABL-INTERACTOR PROTEIN

This is a continuation-in-part of application Ser. No. 08/549,004, U.S. Pat. No. 5,969,101, filed Oct. 27, 1995, the entire contents of which are hereby incorporated by reference.

This application was made with Government support under Grant No. CA 61033 awarded by the National Institutes of Health. The Government has certain rights in the invention.

TECHNICAL FIELD

The present invention relates to a protein that interacts with the cAb1 protein tyrosine kinase and to a nucleic acid sequence encoding same. The invention also relates to complexes of the protein of the invention and cAb1 and to the use of such complexes in the identification of therapeutic and diagnostic agents.

BACKGROUND

The c-Ab1 protein, originally identified as the cellular homolog of the v-ab1 oncogene product of Abelson murine leukemia virus (A-MuLV) (Goff et al, Cell 22:777 (1980); Wang et al, Cell 36:349 (1984)), is a tyrosine kinase of unknown function. Biochemical data suggest that c-Ab1 may regulate signal transduction events in the cytoplasm and processes in the nucleus. c-Ab1 is found primarily in the nucleus (Van Etten et al, Cell 58:669 (1989)), but it is also found in association with the plasma membrane and bound to actin filaments in the cytoplasm (Van Etten et al, Cell 58:669 (1989)); Van Etten et al, J. Cell. Biol. 124:325 (1994)).

The c-Ab1 protein has a complex structure that includes several domains common to proteins implicated in signal transduction pathways. Among these domains are the non-catalytic Src homology 2 and 3 (SH2 and SH3) domains and the tyrosine kinase (SH1) domain. SH2 and SH3 domains are modular components present in a large number of proteins (Pawson, Nature 373:573 (1995)). These domains are critical in the formation of stable signaling protein complexes, and have also been shown to regulate protein function (Feller et al, Trends Biochem. Sci. 19:453 (1994); Cohen et al, Cell 80:237 (1995); Pawson, Nature 373:573 (1995)). The SH3 domain suppresses the intrinsic transforming activity of c-Ab1 in vivo (Franz et al, EMBO J. 8:137 (1989); Jackson and Baltimore, EMBO J. 8:449–456 (1989)), while the SH2 domain is required for the transforming function of activated abl genes (Mayer et al, Mol. Cell. Biol. 12:609 (1992); Mayer and Baltimore, Mol. Cell. Bio. 14:2883 (1994)). The unique carboxy(C)-terminal region of c-Ab1, which is encoded by a single exon, contains several functional and structural domains that include a nuclear localization signal (Van Etten et al, Cell 58:669 (1989)), proline-rich sequences that have the potential to bind to SH3-domain-containing proteins (Feller et al, EMBO J. 13:2341 (1994); Feller et al, Trends Biochem. Sci. 19:453 (1994); Ren et al, Genes & Dev. 8:783 (1994)), a DNA-binding domain (Kipreos and Wang, Science 256:382 (1992)) and an actin-binding domain (Van Etten et al, J. Cell. Biol. 124:325 (1994); McWhirter and Wang, EMBO J. 12:1533 (1993)). Several serine/threonine residues within the C-terminal exon are phosphorylated by the cdc 2 kinase (Kipreos and Wang, Science 248:217 (1990)) and by protein kinase C (Pendergast et al, Mol. Cell. Biol. 7:4280 (1987)). The presence of multiple structural and functional domains within the c-Ab1 tyrosine kinase and its localization to cytoplasmic and nuclear cellular compartments, suggest a potential role for c-Ab1 in the regulation of transcription, DNA replication or cell cycle progression, as well as in the control of signaling events in the cytoplasm.

The tyrosine kinase activity of c-Ab1 is tightly regulated in vivo (Pendergast et al, Proc. Natl. Acad. Sci. USA 88:5927 (1991); Mayer and Baltimore, Mol. Cell. Bio. 14:2883 (1994)). Overexpression of c-Ab1 at levels 5- to 10-fold over the endogenous c-Ab1 protein does not lead to cell transformation but causes growth arrest (Jackson and Baltimore, EMBO J. 8:449 (1989); Jackson et al, EMBO J. 12:2809 (1993); Sawyers et al, Cell 77:121 (1994)). In contrast, structurally altered forms of Ab1 cause cell transformation and exhibit elevated tyrosine kinase activity when expressed at similar levels (Franz et al, EMBO J. 8:137 (1989); Jackson and Baltimore, EMBO J. 8:449 (1989); Muller et al, Mol. Cell. Biol. 11:1785 (1991)).

Activation of the oncogenic potential of c-Ab1 has been shown to occur as a consequence of structural alterations in the amino(N)- or C-terminal sequences (reviewed in Wang, Curr. Opin. Genet. Dev. 3:35–43 (1993)). Three naturally occurring c-ab1-derived oncogenes have been identified (Goff et al, Cell 22:777 (1980); Bergold et al, J. Virol. 61:1193 (1987); Pendergast and Witte, In: Balliere's Clinical Haematology 1(4):1001 (1987); Kurzrock et al, N. Engl. J. Med. 319:990 (1988)). Oncogenic activity has been shown to result from, or be associated with, deletion of the Ab1 SH3 domain and fusion with gag sequences following retroviral transduction (Franz et al, EMBO J. 8:137 (1989); Jackson and Baltimore, EMBO J. 8:449 (1989); Muller et al, Mol. Cell. Biol. 11:1785 (1991)), deletion of Ab1 C-terminal sequences and fusion with viral sequences, while retaining the Ab1 SH3 domain (Bergold et al, J. Virol. 61:1193–1202 (1987)), and fusion of bcr sequences upstream of the second exon of c-ab1 (Muller et al, Mol. Cell. Biol. 11:1785 (1991); McWhirter and Wang, Mol. Cell. Biol. 11:1553 (1991); Pendergast et al, Cell 66:161 (1991)). Mutants of c-Ab1 have also been generated experimentally that exhibit increased transforming activity. These include Ab1 proteins with deletions or alterations in the SH3 and C-terminal sequences (Franz et al, EMBO J. 8:137 (1989); Jackson and Baltimore, EMBO J. 8:449 (1989); Goga et al, Mol. Cell. Biol 13:4967 (1993); Mayer and Baltimore, Mol. Cell. Biol. 14:2883 (1994)). The structural alterations in the mutated Ab1 proteins disrupt the negative regulatory mechanisms that control the c-Ab1 protein tyrosine kinase, generating transforming Ab1 proteins that are constitutively active and are primarily localized in the cytoplasm.

Several possible mechanisms have been suggested for the inhibition of the c-Ab1 tyrosine kinase. Recently, it has been shown that the inhibitory effect of the Ab1 SH3 domain is extremely position sensitive (Mayer and Baltimore, Mol. Cell. Biol. 14:2883 (1994)). These results suggest that, in addition to the SH3 domain, other region(s) of c-Ab1 may be required for repression. Two potential mechanisms have been proposed. First, it is possible that the SH3 domain functions in cis by binding to another region of Ab1 and effectively locking the protein in an inactive conformation. A second model consistent with the available data suggests that the c-Ab1 protein is negatively regulated by a transacting cellular modulator that exerts its effects by interacting with the Ab1 SH3 domain and a second region of the Ab1 protein (Mayer and Baltimore, Mol. Cell. Bio. 14:2883–2894 (1994). The present invention provides such a protein.

SUMMARY OF THE INVENTION

The present invention relates to a protein that interacts with both the SH3 domain and carboxy terminal sequences of the cAb1 tyrosine kinase (ie, it is an Ab1 interactor (Abi) protein). The present protein is a substrate for the cAb1 tyrosine kinase. The protein of the invention contains a SH3 domain and proline-rich sequences critical for binding to cAb1. A basic region in the amino-terminus of the protein of the invention is homologous to the DNA-binding sequence of homeodomain proteins. The properties of the Abi protein indicate that the protein has a dual role as a regulator and effector of the cAb1 protein and that the Abi protein functions as a tumor suppressor in cells.

BRIEF DESCRIPTION OF THE DRAWINGS

FIGS. 1A–1D. Sequence and Northern Blot Analysis of Abi-2

Figure 1D:
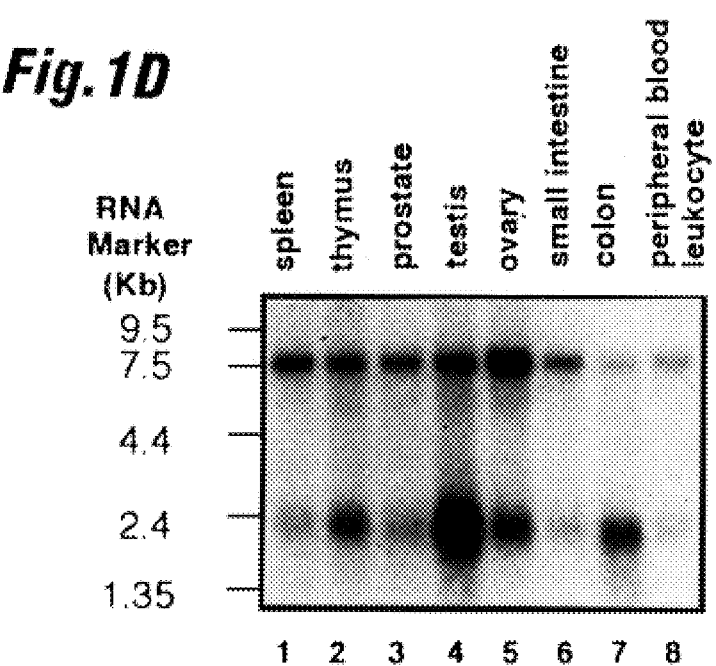

(A) Predicted amino acid sequence of human Abi-2. Sequences in the C terminus corresponding to the SH3 domain are boxed. The three potential SH3 binding sites are in bold and a serine-rich region is in bold and underlined. A potential c-Ab1 tyrosine phosphorylation site is doubly underlined and the tyrosine is marked with an asterisk. Three PEST regions are bracketed with arrows and a homeodomain homologous region at the N-terminus is underlined. A polyproline stretch is underlined with dashed lines (SEQ ID NO:5). (B) Diagram of structural features of Abi-2. (C) Alignment of the Abi-2 homeodomain homologous region with several homeodomains. The consensus sequence is shown at the bottom SEQ ID NO:6, SEQ ID NO:7, SEQ ID NO:8, SEQ ID NO:9, SEQ ID NO:10, SEQ ID NO:11, SEQ ID NO:12, SEQ ID NO:13 and SEQ ID NO:14. (D) Northern blot analysis of abi-2 expression in human tissues. Two micrograms of poly A$^+$ RNA from the indicated human tissues were hybridized to $^{32}$P-labeled full length abi-2 cDNA probe. The RNA markers are indicated at the left.

FIG. 2. Abi-2 encoding sequence. The ATG start and TGA stop codons are marked, as are a potential alternative splice site and the poly A site (SEQ ID NO:15).

FIGS. 3A–3C. Expression and subcellular localization of Abi-2 proteins (A) In vitro transcription and translation of abi-2 cDNA. In vitro transcription/translation was performed without DNA (lane 1), with pGEM vector alone (lane 2), or with pGEM/abi-2 (lane 3). $^{35}$S methionine labeled protein products were separated on SDS-PAGE directly (lanes 1 to 3) or incubated with preimmune serum (lane 4) or anti-Abi-2 serum (lane 5) and the complexes collected on Protein A Sepharose prior to SDS-PAGE separation. Labeled proteins were visualized by fluorography. (B) Expression of Abi-2 in vivo. Bosc 23 cells were transfected with pCGN vector alone (lane 1), or pCGN/abi-2, (lanes 2 and 3). Total cell lysates were separated on SDS-PAGE and subjected to Western blot analysis with an anti-HA monoclonal antibody (lane 2) or anti-Abi-2 antibody (lane 3). For analysis of endogenous Abi-2 expression, lysates from human RAMOS cells (2×10$^5$ cells) were subjected to SDS-PAGE followed by Western blot analysis with anti-Abi-2 antibody (lane 4). The Abi-2 proteins are marked with the arrows. (C) Subcellular localization of Abi-2. Approximately 2×10$^7$ RAMOS cells were swollen in hypotonic buffer for 10 min., and subcellular fractions were prepared. Cell lysates were centrifuged to separate the nuclei from the cytosol/membrane fraction. Equal amounts of total cell lysate, cytosol/membrane, and nuclei were analyzed on an 8% SDS-PAGE, followed by Western blotting with anti-Abi-2 antibodies. The blot was developed with the ECL detection kit.

Figure 4A:
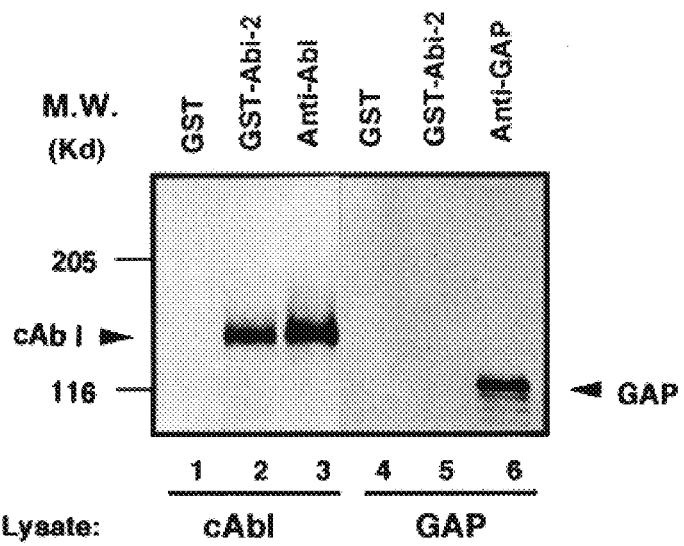
Figure 4B:
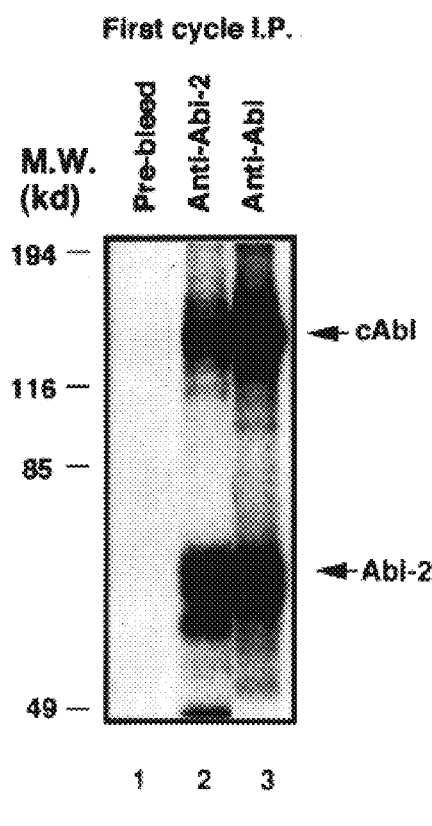
Figure 4C:
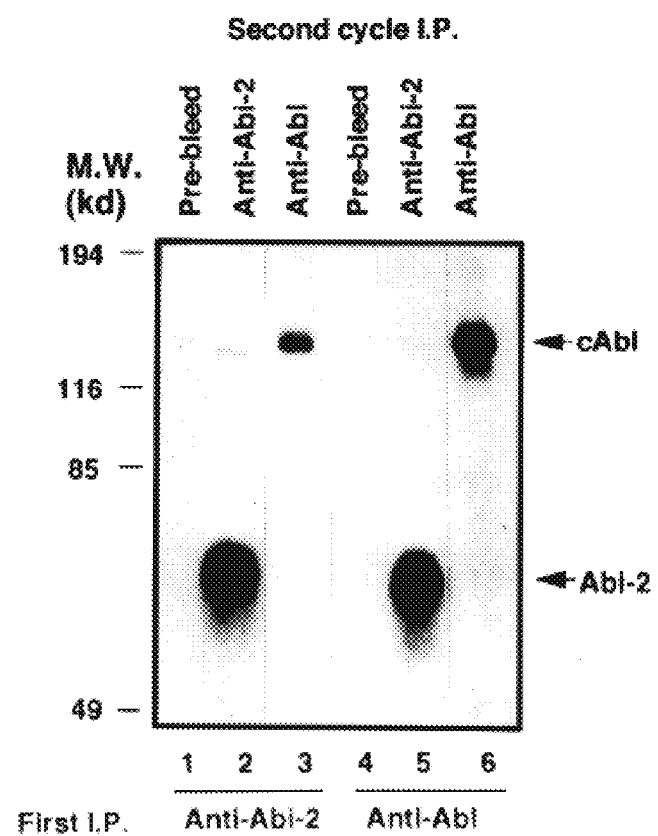

FIGS. 4A–4C. Abi-2 interacts with c-Ab1

(A) Sf9 insect cells were infected with either c-Ab1 or GAP recombinant baculoviruses and labeled with $^{35}$S methionine. Cell lysates were incubated with equal amounts of immobilized GST alone (lanes 1 and 4), GST-Abi-2 (lanes 2 and 5), and anti-Ab1 (lane 3) or anti-GAP (lane 6) antibodies bound to protein A-Sepharose beads. After incubation for 90 min. at 4° C., the beads were washed with RIPA buffer to remove unbound material. Bound proteins were separated on SDS-PAGE and visualized by fluorography. The positions of c-Ab1 and GAP are indicated. (B) Bosc 32 cells co-transfected with the pSRα/c-ab1 and pCGN/abi-2 expression vectors were lyzed and immunoprecipitated with preimmune serum (lane 1), anti-Abi-2 (lane 2), and anti-Ab1 antibodies (lane 3). The immunoprecipitated proteins were subjected to an in vitro kinase assay in the presence of [γ-$^{32}$P]ATP. The phosphorylated proteins were separated on SDS-PAGE and visualized by autoradiography. (C) Following immunoprecipitation (I.P.) and kinase assay as described in B, the bound proteins were eluted from the immune complexes by boiling in the presence of SDS-PAGE sample buffer and subjected to a second cycle I.P. with the indicated sera. Proteins immunoprecipitated by the second cycle I.P. were separated on SDS-PAGE and visualized by autoradiography.

FIGS. 5A–5D. Abi-2 binds to c-Ab1 at both SH3 and C-terminal regions (A) Interaction of Abi-2 with c-Ab1 is retained following deletion of the c-Ab1 SH3 domain. Lysates of Cos cells transfected with expression vectors encoding wild type c-Ab1 (pSRα/c-abl) (lanes 1–3) or an SH3 deletion mutant of c-Ab1 (pSRα/c-ab1ΔSH3) (lanes 4–6) were incubated with immobilized GST alone (lanes 1, 4), GST-Abi-2 (lanes 2, 5), or anti-Ab1 antibodies bound to Protein A-Sepharose beads (lanes 3, 6). Bound proteins were separated on SDS-PAGE, transferred to nitrocellulose, and immunoblotted with anti-Ab1 antibodies. Proteins were visualized as described in FIG. 3. (B) Mapping of the Abi-2 binding sites on c-Ab1. Wild type c-Ab1 (top) and c-Ab1 deletion mutants are schematically shown. Binding of c-Ab1 fragments to Abi-2 was determined either by the yeast two-hybrid system assay or by an in vitro binding assay, as indicated to the right.

NLS: nuclear localization sequence; BD: binding domain. (C) Deletion of the Ab1 SH3 domain and Ab1-C-terminal proline-rich sequences abolishes Ab1 binding to Abi-2. The indicated in vitro translated proteins were labeled with $^{35}$S methionine and incubated with GST alone, GST Abi-2, and anti-Ab1 antibodies bound to Protein A-Separose beads, as indicated. After incubation for 60 min. at 4° C., the complexes were washed and bound proteins were analyzed by SDS-PAGE. $^{35}$S labeled proteins were visualized by fluorography. (D) The binding of Abi-2 to the Ab1 SH3 domain is specific. abi-2 cDNA was subcloned into pAS1-CYH2 and expressed in yeast as a GAL4 DB-fusion which contains the influenza hemagglutinin (HA) epitope tag. Yeast cell lysates were incubated with GST or GST-fusion proteins as indicated. Bound proteins were separated on a 10% SDS-PAGE, transferred to nitrocellulose, and analyzed by Western blotting using anti-HA antibody. The arrow indicates the HA-tagged Abi-2 protein.

Figure 6A:
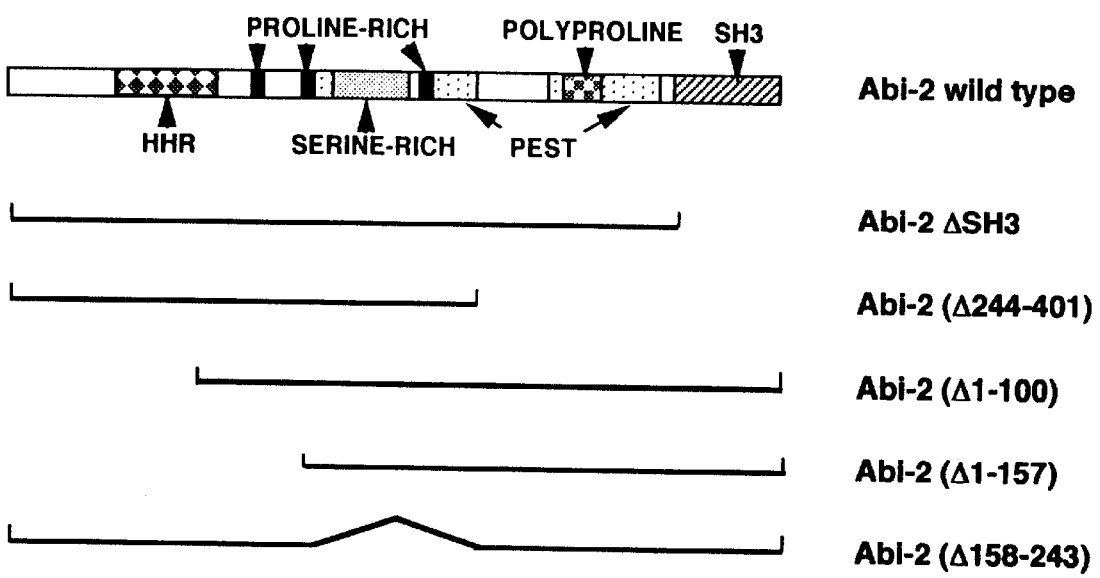

FIGS. 6A–6C. c-Ab1 binds to the proline-rich N-terminus and the C-terminal SH3 domain of Abi-2

(A) Schematic representation of the Abi-2 deletion mutants constructed. (B) cDNAs encoding abi-2, abi-2ΔSH3, and abi-2Δ244-401 were subcloned into the pGEM vector for in vitro transcription/translation. The $^{35}S$ methionine translated proteins were incubated with anti-Abi-2 antibodies bound to Protein A (lanes 1, 4 and 7), GST-Ab1 SH3 (lanes 2, 5 and 8), and GST-Ab1 (593–730) (lanes 3 and 6). Bound proteins were washed and separated on SDS-PAGE and $^{35}S$ labeled proteins were visualized by fluorography. (C) To map the region in Abi-2 that binds to Ab1 SH3 domain, cDNAs encoding N-terminal deletion mutants (abi-2Δ1-100 and abi-2Δ1-157) or an internal deletion (abi-2Δ158-243) of Abi-2 were subcloned in frame into pCGN vector and expressed as HA-tagged proteins in Cos cells by transient transfection. Cell lysates were prepared at 2½ days post-transfection and the lysates were incubated with GST alone (lanes 1, 4 and 7), GST-Ab1 SH3 (lanes 2, 5 and 8), and GST-Ab1 (593–730) (lanes 3, 6 and 9). Bound proteins were separated on SDS-PAGE, transferred to nitrocellulose, and analyzed by Western blotting with the anti-HA monoclonal antibody.

FIGS. 7A and 7B. Abi-2 is phosphorylated in vitro and in vivo by c-Ab1

(A) In vitro phosphorylation: Immobilized GST alone (lanes 1, 3 and 5) or GST-Abi-2 (lanes 2, 4 and 6) was incubated at 4° C. for 60 min. with in vitro transcription/translation products (bottom panel) of c-Ab1 wild type (lanes 1 and 2), c-Ab1 K290R (lanes 3 and 4) and c-Ab1ΔSH3Δ544-637 (lanes 5 and 6). Bound proteins were subjected to in vitro phosphorylation at 30° C. in the presence of [γ-$^{32}P$]ATP and MnCl$_2$. The phosphorylated proteins bound to beads were washed three times, separated on SDS-PAGE and visualized by autoradiography. (B) In vivo phosphorylation: Bosc 23 cells were transfected with pCGN vector alone (lane 1), pSRα/c-ab1 (lane 2), pCGN/abi-2 (lane 3), and pSRα/c-ab1 plus pCGN/abi-2 (lane 4). Cell lysates were separated on SDS-PAGE, transferred to nitrocellulose, and immunoblotted with the indicated antibodies. Immunoreactive proteins were visualized by ECL.

FIGS. 8A–8D. Expression of an Abi-2 mutant deficient in binding to the Ab1 SH3 domain activates the tyrosine kinase and transforming properties of c-Ab1

(A) Expression of abi-2Δ1-157 in NIH3T3 cells. Cells were transfected with pCGN alone (lane 1) or pCGN/abi-2Δ1-157 (lane 2). Following hygromycin selection, approximately 2×10$^5$ cells were lysed in sample buffer and subjected to Western blot analysis using anti-HA antibody. The Abi-2Δ1-157 protein is indicated with the arrow. (B) Abi-2Δ1-157 reverses biologic selection against c-Ab1 overexpression. NIH3T3 cells expressing Abi-2Δ1-157 or vector control were infected with retroviruses encoding the neo resistance gene alone or with c-ab1 wild type or c-ab1K290R as indicated- After 2½ days, cells were selected with G418. The left panels show anti-Ab1 Western blots of infected cells at 2½ days (top) or 22 days post-infection (bottom). c-Ab1 is indicated by the arrow. The right panel shows an anti-pTyr Western blot of the infected cells at 22 days post-infection. (C) Abi-2Δ1-157 activates the c-Ab1 transforming activity. NIH3T3 cells were transfected with either pCGN vector (panels 1 to 3) or pCGN/abi-2Δ1-157 (panels 4 to 6). After selection with hygromycin, the cells were infected with retroviruses expressing neo (1 and 4), wild type c-Ab1 (2 and 6), c-Ab1 K290R (5), or v-Ab1 (3). At 2½ days post-infection the cells were incubated with media containing G418 and maintained under drug selection for 22 days. Morphological transformation was clearly observed in c-Ab1 infected NIH3T3 cells that had been transfected with Abi-2Δ1-157 but not in cells expressing vector control (compare panels 2 and 6). (D) A model is proposed for the interaction of c-Ab1 and Abi-2 and the presence of c-Ab1/Abi-2 complexes in unphosphorylated and tyrosine phosphorylated states. Activation of the c-Ab1 tyrosine kinase leading to tyrosine phosphorylation of Abi-2 may occur by a variety of events, some of which are listed in the box.

Figure 9A:
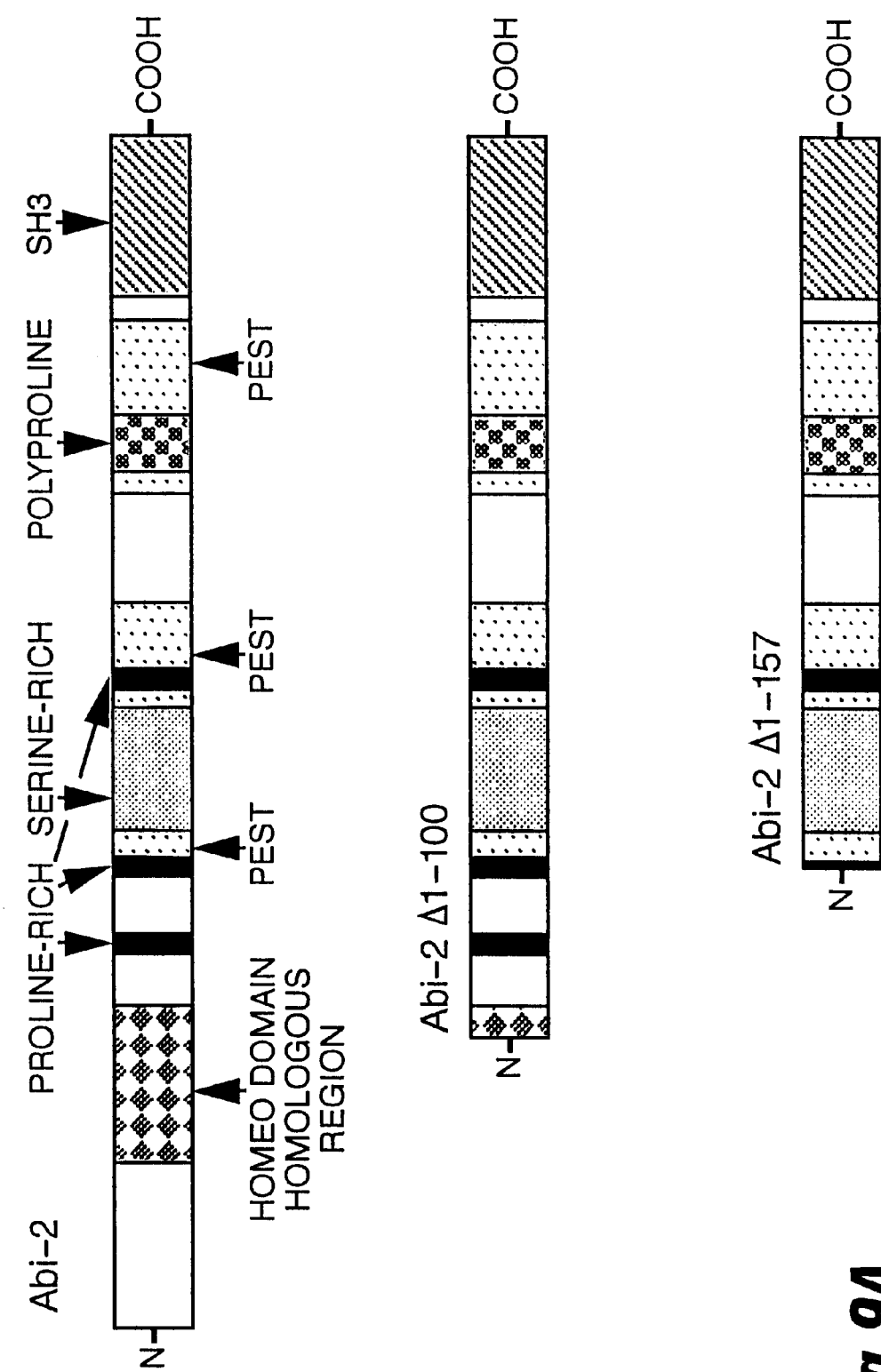
Figure 9B:
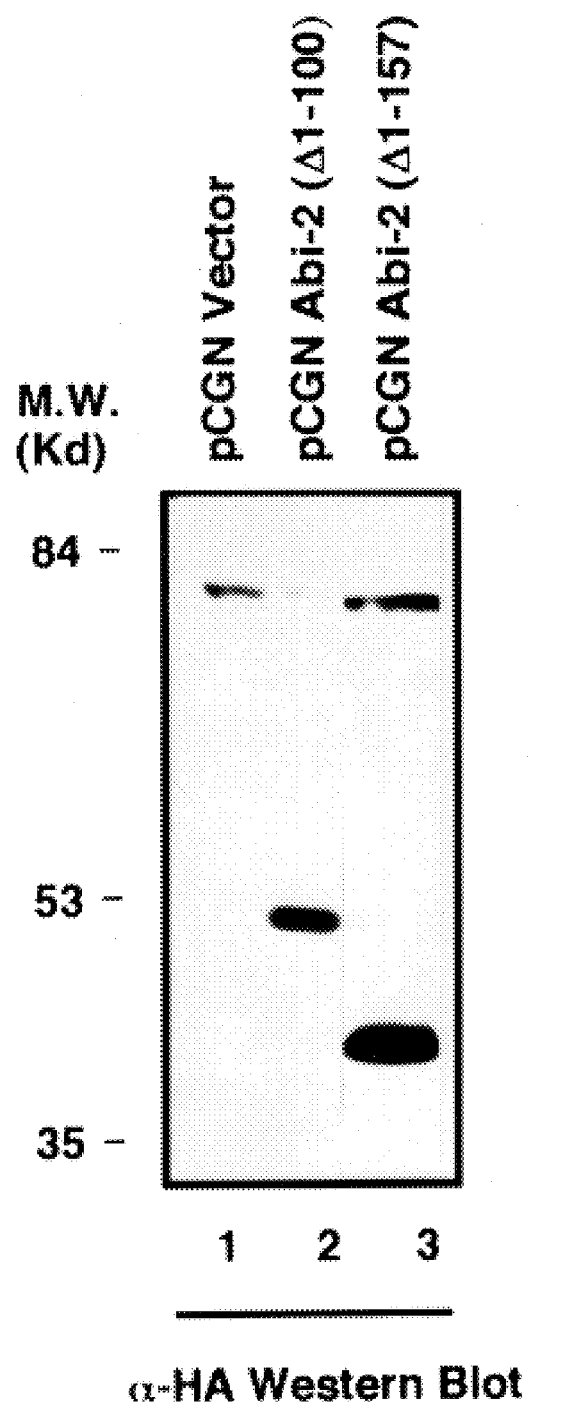

FIGS. 9A–9C. Effect of Abi-2 deletion mutants on BCR/Ab1 transforming activity.

(A) Diagram of the structural domains present in full length Abi-2 and truncated Abi-2 proteins (Abi-2Δ1-100 and Abi-2Δ1-157).

(B) The expression of Abi-2 deletion mutants in Cos cells is shown. Cos cells were transfected with vector alone (lane 1), pCGN/abi-2Δ1-100 (lane 2) or pCGN/abi-2Δ1-157 (lane 3) and subjected to Western blot analysis with anti-HA monoclonal antibody to detect the expression of HA-tagged Abi-2 mutants.

(C) Rat1 cells transformed by p185 BCR/Ab1 were transfected with the indicated constructs. After five days of selection with hygromycin, the cells were plated in soft agar. The relative transforming activity was calculated by counting the number of colonies that grew in soft agar three weeks after plating.

Figure 10:
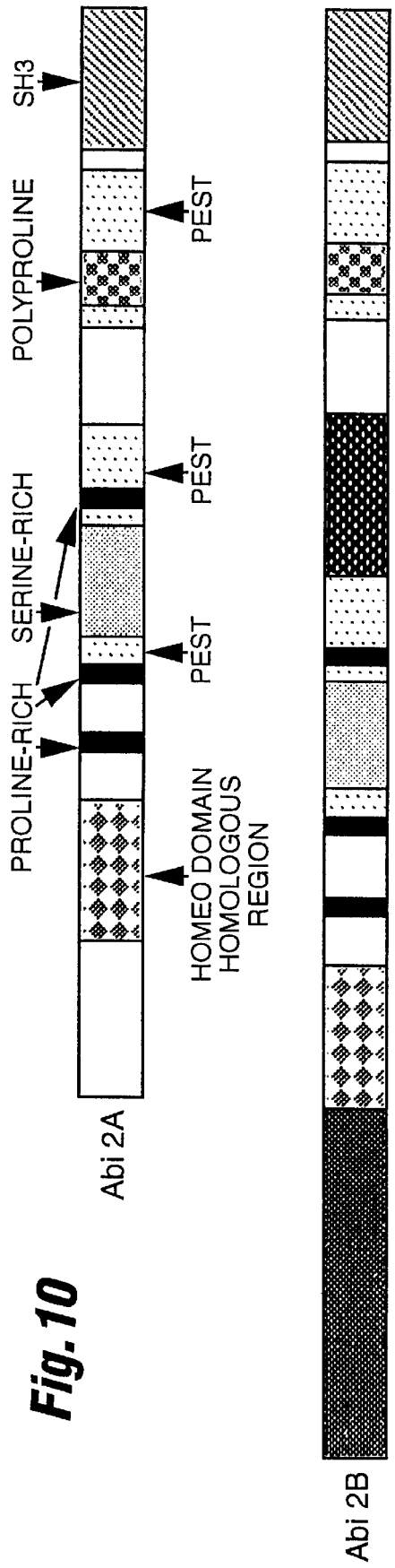

FIG. 10. Multiple Abi-related proteins may be expressed in mammalian cells.

Figures 11, 13:
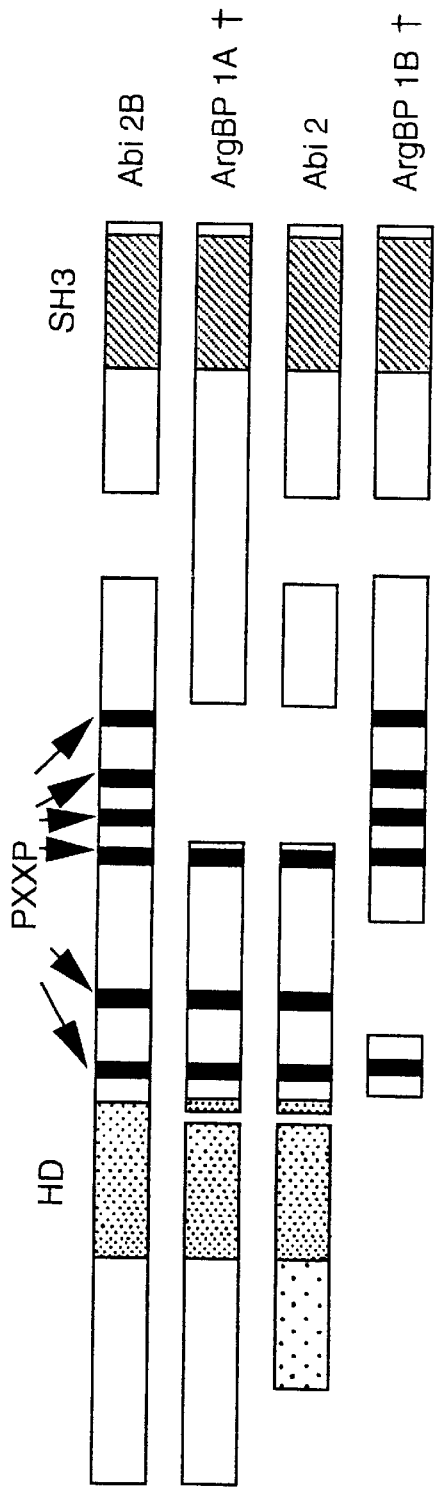

FIG. 11. Multiple alternatively spliced forms of Abi-2 may be expressed in mammalian cells. †=cloned by Wang et al (oncogene 12:1921 (1996)). HD=homeodomain homologous region; SH3=Src homology 3 domain.

Figure 12:
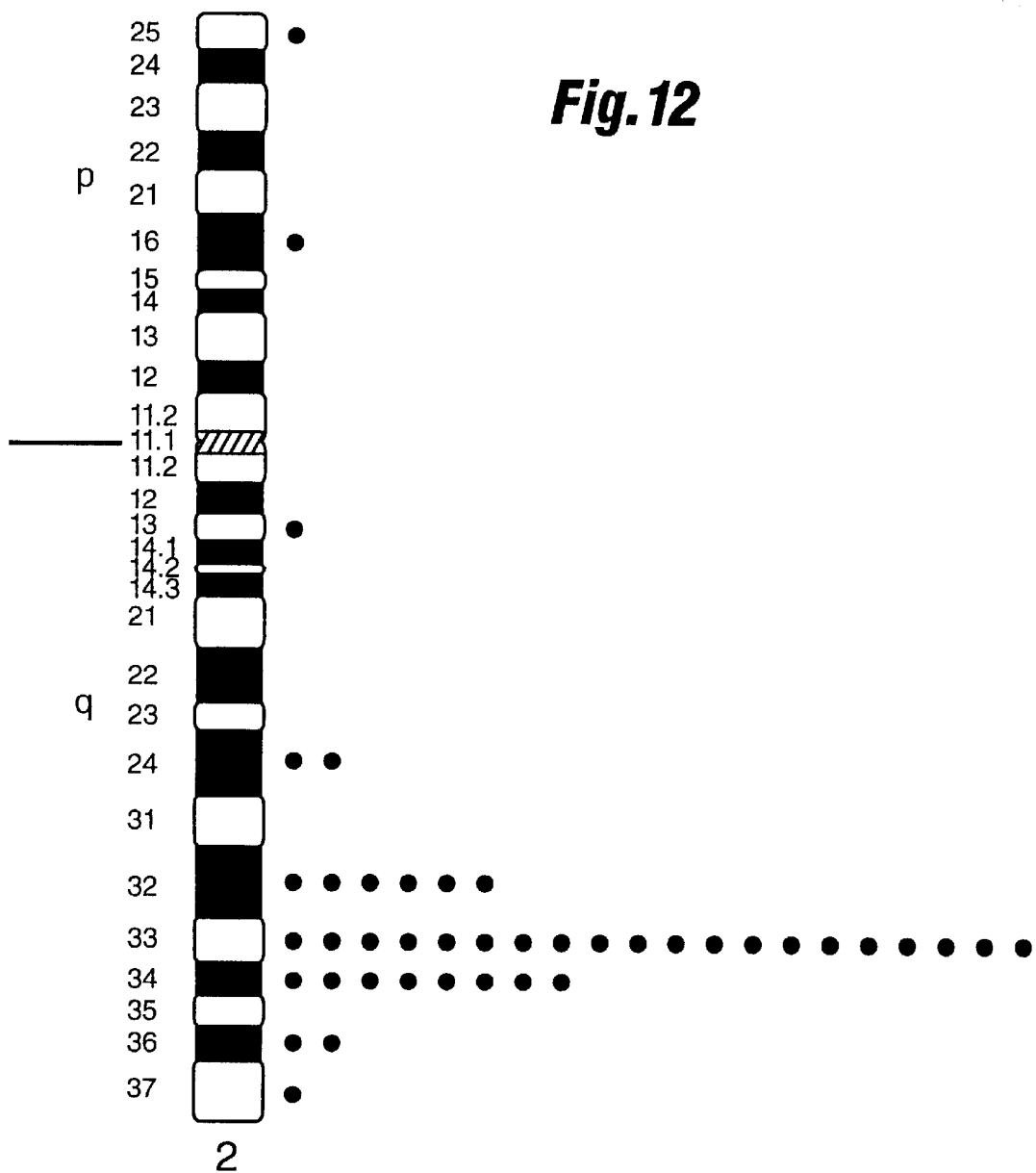

FIG. 12. Chromosomal assignment of Abi-2 to human chromosome 2q33.

FIG. 13. Correlation of human sequences detected by Abi-2 cDNA with human chromosomes in rodent X human somatic cell hybrids.

DETAILED DESCRIPTION OF THE INVENTION

The present invention relates to a novel Ab1-interactor (Abi) protein and to a nucleic acid sequence encoding same. The Abi protein of the invention belongs to a family of SH3-containing, proline-rich proteins that interact with and/or become phosphorylated by specific cytoplasmic tyrosine kinases. The present protein interacts with multiple domains of Ab1 and is a substrate for Ab1 tyrosine kinase activity. The discovery of the Abi protein of the invention provides new approaches to decifering the mechanism of Ab1-induced carcinogenesis and to detecting, diagnosing and treating cancers, including leukemias, breast cancer, prostate cancer and colon cancer.

The SH3 domain of the Abi protein of the invention is at the C-terminus (see, for example, aa 346–397 of the Abi protein shown in FIG. 1, A, designated Abi-2). Several proline-rich stretches are present (FIG. 1, B) that constitute binding sites for SH3 domain-containing proteins and contain the consensus PXXP (SEQ ID NO:16) sequence that is present in all high affinity SH3 ligands identified to date (Cohen et al, Cell 80:237 (1995); Rickles et al, EMBO J. 13:5598 (1994)). A polyproline stretch is present upstream of the SH3 domain which could function as a transcriptional activation domain (Tanaka et al, Mol. Cell. Biol. 14:6046 (1994)). Sequences enriched in serine/threonine, glutamate/aspartate and proline residues, designated PEST regions, are also found in the present protein. PEST regions are identified in the central and C-terminal portions of the Abi protein (see FIG. 1, B). The N-terminal region of the present protein is basic (eg, calculated pI about 11.4) and homologous to the DNA-binding sequence of homeodomain proteins (the protein of the invention is unique among the family to which it relates in having both an SH3 domain and a homeodomain homologous region). The C-terminal portion of the protein is acidic (eg, pI about 3.5). A serine-rich region is present in the central portion of the protein (see FIG. 1, B). The Abi protein contains several (eg 9) serine/threonine residues followed by proline, indicative of phosphorylation by proline-directed protein kinases (Kemp and Pearson, Trends Biochem. Sci. 15:342 (1990)). Certain sites conform to the cdc 2 kinase consensus sequence Ser/Thr-Pro-X-basic (Moreno and Nurse, Cell 61:549 (1990)). There are also potential cAMP-dependent protein kinase sites (eg 11) and potential protein kinase C sites (eg 9) (Kemp and Pearson, Trends Biochem. Sci. 15:342 (1990)). Several tyrosines in the sequence are found in peptides that correspond to optimal peptide substrates for the Ab1, Fps and Src protein tyrosine kinases (Songyang et al, Nature 373:536 (1995)).

A specific embodiment of the protein of the invention relates to a human Abi, for example, the protein designated Abi-2 having the amino acid sequence shown in FIG. 1,A, or alternative spliced forms thereof (see splice site noted in FIG. 2). In addition to the FIG. 1,A sequence, human Abi sequences include allelic variations, eg naturally occurring allelic variations, of the FIG. 1,A sequence. The variant sequences retain the functional characteristics of the FIG. 1,A sequence and the structural characteristics shown in FIG. 1,B. By way of example, it is noted that FIG. 1,C illustrates variations that might be present in the N-terminal homeodomain-like homologous region of the present protein.

The present invention relates not only to the entirety of the Abi protein, for example, the FIG. 1,A sequence or allelic variations thereof, but to portions thereof as well. The term "portions" relates to peptides and polypeptides of at least 10 or at least 16–18 amino acids in length, preferably, at least 30 or at at least 50 amino acids, more preferably at least 100 amino acids and most preferably at least 300 amino acids. Examples of such portions include subsequences of the protein of the invention that comprise amino acid sequences corresponding to one or more of the domains depicted in FIG. 1,B, particularly, the SH3 domain (eg about amino acids 360–397 of the FIG. 1,A sequence), the tyrosine phosphorylation site (eg about amino acids 320–327 of the FIG. 1,A sequence) or the homeodomain homologous region (eg about amino acids 55–117 of the FIG. 1,A sequence), alone or in combination. The polypeptides Abi-2Δ1-100 and Abi-2Δ1-157 represent further examples of such portions.

In addition to the Abi protein, the present invention also relates to a nucleic acid sequence (DNA or RNA) encoding Abi, eg human Abi, and to fragments thereof suitable for use, for example, as probes or primers, of at least 15, preferably at least 30, more preferably at least 90, 150, 300, or 900 bases in length that encode the "portions" (eg domains) described above. In a specific embodiment, the invention relates to a nucleic acid sequences encoding the FIG. 1,A amino acid sequence, alternative spliced forms thereof and portions thereof. In particular, the present invention relates to the FIG. 2 nucleic acid sequence or fragments thereof (particularly that portion encoding Abi-2) or to a nucleic acid sequence substantially identical to the nucleic acid sequence of FIG. 2. A "substantially identical" sequence is one the complement of which hybridizes to the nucleic acid sequence of FIG. 2 in 6×saline/sodium citrate (SSC) containing 5×Denhardt's reagent, 0.5% SDS, 100 μg/ml denatured salmon sperm DNA, and which remains bound when subjected to washing at 68° C. to 42° C. with 2×SSC containing 0.5% SDS. (For details of reagent preparation, etc, see Sambrook et al, Molecular Cloning, A Laboratory Manual, 2nd Edition). The invention also relates to nucleic acids complementary to those described above.

The present invention also relates to a recombinant molecule (a construct) comprising a nucleic acid sequence as described above and to a host cell transformed therewith. Using methodologies well known in the art, a recombinant molecule comprising a vector and a nucleic acid sequence encoding the Abi protein of the invention, or portion thereof as defined above, can be constructed. Vectors suitable for use in the present invention include plasmid and viral vectors, for example, pGEX3X, PGEM, pAcGHLT, pCGN, pSRα, pSRαMSVtKneo and pJRΩ. Appropriate vectors can be selected based on their compatibility with transformation into a selected host cell. The nucleotide sequence of the invention can be present in the vector operably linked to regulatory elements, for example, a promoter. Suitable promoters include, but are not limited to the SP6, T7, polyhedrin CMV, SRα, LTR and MMTV LTR promoters.

As indicated above, the recombinant molecule of the invention can be constructed so as to be suitable for transforming a host cell. Suitable host cells include prokaryotic cells, such as bacteria, lower eukaryotic cells, such yeast, and higher eukaryotic cells such as mammalian cells and insect cells. The recombinant molecule of the invention can be introduced into appropriate host cells using a variety of known methods.

The present invention further relates to a method of producing the Abi protein of the invention, or portions thereof as defined above. The method comprises culturing the above-described transformed host cells under conditions such that the encoding sequence is expressed and the protein thereby produced.

The Abi protein of the invention, or portions thereof as defined above, can be present in isolated form, for example, substantially free of proteins with which it is normally associated. Advantageously, the protein is at least 90% pure, more preferably at least 95% pure (as determined by gel electrophoresis using an appropriate stain (eg coomassie blue or silver)). The proteins, polypeptides and peptides of the invention can be produced recombinantly using the nucleic acid sequences as described above, or chemically using known methods. When prepared recombinantly, the protein of the invention can be produced alone or as a fusion product, for example, fused with a protein such as glutathione-S-transferase (GST) or hemagglutinin (HA). For example, the coding sequence of the invention (eg the sequence encoding the human Abi) can be cloned in frame with a sequence encoding another protein (such as GST) and the fusion product expressed in an appropriate host cell (see FIGS. 3, 4 and 5 and disclosure relating thereto).

The proteins, polypeptides and peptides of the invention can be used as antigens to generate Abi specific antibodies, particularly, antibodies specific for human Abi (eg Abi-2). Methods of antibody generation are well known in the art. Both monoclonal and polyclonal antibodies are contemplated, as are antigen binding fragments thereof. Chimeric antibodies (eg humanized antibodies) are also within the scope of the invention, appropriate splicing techniques being known in the art. One skilled in the art will appreciate that such antibodies (which can be labeled with a detectable label) can be used to selectively identify and isolate the proteins of the invention, including mutant and/or phosphorylated (or unphosphorylated) forms of the Abi protein.

The results presented in the Examples that follow demonstrate that the protein of the invention, for example, Abi-2, forms a complex with c-Ab1 through direct contact with both the SH3 and C-terminal domains of c-Ab1. Examination of the phosphorylation state of the endogenous c-Ab1/Abi-2 complexes in unstimulated cells reveals that neither protein is tyrosine phosphorylated. Overexpression of c-Ab1, however, leads to c-Ab1 activation and tyrosine phosphorylation of the co-expressed Abi-2 protein in vivo. While not to be viewed as limiting, a model is presented in FIG. 8D for the existence of unphosphorylated and tyrosine-phosphorylated c-Ab1/Abi-2 complexes.

The Abi protein (for example, Abi-2) may function to stabilize the inactive form of c-Ab1 or block access to critical cellular protein substrates of the c-Ab1 tyrosine kinase. A second role for the Abi protein of the invention is that of effector of the c-Ab1 protein tyrosine kinase. At least two tyrosines within Abi are found in sequences predicted to be optimal peptide substrates for the c-Ab1 tyrosine kinase (Songyang et al, Nature 373:536 (1995)). In the case of Abi-2, the optimal phosphorylation site corresponds to the tyrosine in the sequence YSDP just upstream of the SH3 domain (see FIG. 1,A). These results indicate that the Ab1 SH3 and C-terminal domains play a role in substrate recruitment.

In addition to the dual SH3-proline interactions within the c-Ab1/Abi complex, contacts may be made between tyrosine phosphorylated sequences in Abi (eg Abi-2) and the Ab1 SH2 domain. It has been shown that protein tyrosine kinases preferentially phosphorylate peptide sequences that bind with high affinity to their own SH2 domains (Songyang et al, Nature 373:536 (1995)). This type of interaction may protect Abi-2 from dephosphorylation and strengthen the interaction between Abi-2 and c-Ab1.

Expression of an Abi mutant protein that lacks the N-terminal homeodomain homologous region but retains the two domains implicated in binding to the Ab1 SH3 domain and Ab1 C-terminal sequences (eg Abi-2Δ1-100 (see FIG. 9)), has been shown to inhibit the transforming activity of the Ab1 oncoprotein. It has also been shown that expression of an Abi mutant that lacks the sequences required for Ab1 SH3 domain binding while retaining binding to the C-terminal region of Ab1 (eg Abi-2Δ1-157 (see FIG. 9)) does not inhibit Ab1-transforming activity, in fact, exerts a stimulatory effect.

The effect of an Abi mutant protein on normal cAb1 tyrosine kinase has also been examined (see FIG. 8, Table 1). The Abi-2Δ1-157 mutant activates the tyrosine kinase and transformation activities of cAb1 in cells. The mutant protein may simply displace the endogenous Abi-2 protein and thereby allow constitutive phosphorylation of other protein targets by the c-Ab1 tyrosine kinase. Alternatively, binding of the mutant protein to the Ab1 C-terminus may activate its tyrosine kinase activity and transforming potential. These two possibilities may not be mutually exclusive. An additional mechanism whereby the mutant could elicit transformation is by retaining c-Ab1 in the cytoplasm and thereby keeping c-Ab1 outside of the nucleus. It has been proposed that the growth inhibitory activity of overexpressed c-Ab1 requires localization to the nuclear compartment (Sawyers et al, Cell 77:121 (1994)).

The identification of the Abi protein of the invention as a substrate of the c-Ab1 tyrosine kinase which, like c-Ab1, is found in the cytoplasm and the nucleus, and the finding that alterations in Abi can activate the c-Ab1 transforming potential, provides new directions in the investigation of c-Ab1 functions and indicates a role for Abi in cancer. For example, mutations or deletions in Abi may be associated with the progression of Philadelphia-chromosome positive human leukemias from the chronic to the blast crisis phases of the disease. Alterations in Abi-2 may also be linked to the development of other leukemias and other forms of cancer. Abi proteins of the invention, and mutant forms thereof including the truncated forms described above, can be used to design or identify therapeutic agents (eg mimetics) that stabilize Ab1 in a non-transforming form or specifically inhibit the transforming activity of oncogenic forms of the Ab1 tyrosine kinase.

It is noteworthy that the protein of the invention and HSI (Taniuchi et al, The EMBO J. 14:3664 (1995); Fukuda et al, Proc. Natl. Acad. Sci. USA 92:7302 (1995)) share certain structural similarities. Accordingly, functional similarities (eg role in B cell responsiveness and apoptosis) may also be shared. That being the case, it is contemplated that the protein of the invention, or appropriate portions thereof (eg those structurally similar to HSI), or mimetics thereof, can be used to modulate B cell responses. By way of example, it may be possible to transiently induce expression ex vivo to effect the conversion of stem cells to B cells.

The data provided in the Examples that follow demonstrate that alterations in the Abi protein of the invention can result in a deregulation of cAb1 function as evidenced by results of transformation assays. Accordingly, the identification of mutations, deletions, amplifications or chromosonal rearrangements of the Abi protein of the invention can bemused as an indicator of a neoplastic or preneoplastic condition. Such alterations can be detected, for example, by comparing DNA, RNA and/or protein from tumor (or preneoplastic) tissue or cells with normal tissue or cells. Sequencing of the Abi gene from such tissue, when necessary or advantageous, can be carried out, for example, using PCR or single-strand conformation polymorphism. Protein sequencing can be carried out using known techniques. Further examination of the Abi protein in such tissue or cell samples can be used to determine the state of tyrosine phosphorylation (eg using Western blotting with antiphosphotyrosine antibodies). An increase in Abi tyrosine phosphorylation may be indicative of deregulation of cAb1 function. In this regard, cAb1 protein can be immunoprecipitated from lysates of tumors (or suspected preneoplastic tissue) and normal tissues and subjected to in vitro kinase assays with the Abi protein of the invention (eg GST-Abi-2) or portions thereof containing the tyrosine phosphorylation site (in this regard, see description above of the tyrosine phosphorylation site of the Abi-2 protein and Kharbanda et al, Nature 376:785 (1995)). Activation of the intrinsic cAb1 tyrosine kinase results in enhanced phosphorylation of the substrate.

FIGS. 10 and 11 show the alternatively spliced forms of Abi-2 (an alternatively spliced form being designated Abi-2A). In FIG. 11, four alternatively spliced forms of Abi-2 are shown and aligned.

Arg BP1A and Arg BP 1B were cloned and sequenced by Wang et al, Oncogene 12:1921 (1996). These molecules were identified by Wang et al in a screen for proteins that bound to the cAb1-related kinase, Arg. Two cAb1 binding sites, a N-terminal PXXP (SEQ ID NO:16) sequence and a C-terminal SH3 domain, exist in all four proteins. The N-terminal sequence of Abi-2 (dotted box) is specific because an insertion of an Abi-2 specific exon results in differential usage of the translation codon. The existence of the alternatively spliced forms of Abi-2 offers the possibility that the different forms serve purposes, eg that of an antagonist of cAb1 kinase or that of an activator of cAb1 kinase. That being the case, the expression of a specific form or forms may reflect a disease state, such as cancer.

The gene for human Abi-2 has now been mapped to human chromosome 2q33. Mutations in this region can serve as markers for disease, including cancer.

The Abi protein and the various alternatively spliced forms of Abi-2 of the invention may also exhibit an altered subcellular localization in preneoplastic or neoplastic tissue (such is known to be the case for p53 in breast cancer—see Moll et al, Proc. Natl. Acad. Sci. USA 89:7262 (1992)). Immunocytochemical analysis, for example, using affinity purified anti-Abi-2 antibodies, can be performed to determine whether the localization of Abi protein in the suspected tissue is different from that of adjacent normal tissue.

As indicated above, the present invention includes within its scope methods of using the proteins, polypeptides and peptides of the invention (eg, recombinantly produced human Abi or portions (eg domains) thereof) to screen compounds for their ability to affect (eg inhibit) Ab1 oncogenic activity, for example, by stabilizing the cAb1 inactive conformation or by blocking access of cAb1 to its natural substrates. In one type of screening assay, compounds are tested for their ability to alter (eg inhibit) Ab1 transforming activity. For example, cells (eg NIH 3T3 cells) expressing both a cAb1 encoding sequence and a sequence encoding a protein of the invention that converts cAb1 into a transforming protein (eg an N-terminal truncated form of human Abi such as Abi-2Δ1-157) can be contacted with a compound the transformation-altering activity of which is to be tested. An inhibition of the transforming activity of cAb1 (eg as determined by a reduction in the number of colonies having a transformed morphology) is indicative of a compound that is an inhibitor of cAb1-induced transformation and thus a compound potentially useful as a cancer chemotherapeutic agent. Based on this type of screen, compounds can be identified that mimic intact Abi, for example, by restoring Ab1 to its inactive conformation and stabilizing it in that form.

The invention further relates to a screen for testing the ability of a compound to effect transformation. In accordance with this screen, cells containing potentially oncogenic cAb1 and an Abi protein of the invention or portion/mutant thereof that inhibits the oncogenic potential of the cAb1, are contacted with a compound the transforming activity of which is to be tested. Transformation of the cells upon that contact is indicative of a potentially carcinogenic agent. Such agents may act by displacing the Abi protein of the invention from the Abi/cAb1 complex.

Studies described in the Examples that follow demonstrate that expression of specific forms of the Abi protein of the invention can block the transforming activity of oncogenic Ab1 proteins. Accordingly, the invention includes within its scope a gene therapy approach to cancer treatment that involves introduction into cells, for example, tumor cells, of a nucleic acid sequence encoding the Abi protein of the invention, or portion/mutant thereof that blocks Ab1 transforming activity, under conditions such that the protein is produced and the Ab1 transforming activity thereby blocked. Portions of the Abi protein suitable for use in such therapy can be determined in vitro using cultured cells that represent a suitable model for the target tumor and transformation assays known in the art (eg growth in soft agar). Introduction of the nucleic acid into the target tissue can be effected using a delivery system selected based on the nature of the target tumor (for example, delivery can be effected using liposomes or expression vectors including viral vectors such as retroviruses, adeno- and adenoassociated viruses, herpes viruses, vaccine viruses and the like).

Also included within the scope of the invention are pharmaceutical compositions comprising the proteins, polypeptides or peptides, of the invention and compounds selected using the above-described screening protocols. In addition to the active agent, such compositions can include a pharmaceutically acceptable carrier, encapsulating agent (eg liposome), etc. The amount of active agent in the composition can vary with the agent, the patient and the effect sought. Likewise, the dosage regimen used will vary depending on the composition and the disease/disorder to be treated. Depending on the specific condition being treated and the formulation used, administration can be effected locally or systemically. Routes of administration include parenteral (eg intramuscular, subcutaneous, intravenous, intraperitoneal, intranasal or intraocular), oral, rectal, transmucosal and intestinal.

The invention also includes within its scope kits suitable, for example, for use in carrying out the screening methodologies described above. Such kits can include nucleic acid sequences encoding the Abi protein of the invention, or portions thereof as described above, disposed within a container means. Alternatively, kits can include the peptide, polypeptide or protein of the invention. Such kits can be suitable for use in the analyses described above.

Certain aspects of the present invention are described in greater detail in the non-limiting Examples that follow.

EXAMPLES

The experimental protocols and materials described below are referenced in the specific Examples that follow.

Cells and Viruses

Recombinant c-Ab1 baculovirus was prepared as described (Pendergast et al, Cell 66:161 (1991)). Recombinant GAP baculovirus (Trahey et al, Science 242:1697 (1988)) was obtained from Dr. R. Clark and Dr. F. McCormick. Bosc 23 cells, obtained from Drs. W. S. Pear and D. Baltimore (Pear et al, Proc. Natl. Acad. Sci. USA 90:8392 (1993)), were grown in DMEM with 10% fetal calf serum (FCS); COS cells were grown in DMEM plus 5% FCS; RAMOS cells were grown in RPMI 1640 plus 10% FCS; Sf9 insect cells were grown in Grace Media plus yeastolate and 10% FCS.

Antibodies

Polyclonal antibodies against Abi2 were prepared by immunization of New Zealand White female rabbits with a-GST-Abi-2 fusion protein. Polyclonal antibodies and a mouse monoclonal anti-Ab1 antibody were previously described (Pendergast et al, Oncogene 4:759 (1989); Konopka et al, Cell 37:1035 (1984); Pendergast et al, Cell 66:161 (1991)). Antibodies against Ras GAP were obtained from Drs. R. Clark and F. McCormick. Monoclonal antibody against HA (12CA5) was purchased from Boehringer Mannheim. Monoclonal antibody against phosphorylated tyrosine (PY69) was obtained from ICN Biochemicals Inc.

Plasmid Constructions

A cDNA fragment encoding the c-Ab1 SH3 domain (amino acids 47–147) was excised from pGEX3X (929–1029) P210 [SH3] (Pendergast et al, Cell 66:161 (1991)) by Bam H1/Aat II restriction enzyme digestion and subcloned in frame into pPC62 (obtained from P. M. Chevray) (Chevray and Nathans, Proc. Natl. Acad. Sci. USA 89:5789 (1992)). The resultant plasmid, designated pPC60/ab1SH3, directs the synthesis of a fusion protein containing the Gal 4 DNA binding domain and the SH3 domain of c-Ab1 when expressed in yeast. The pPC60/ab1SH3 plasmid was used as the bait in the two-hybrid screening in yeast.

The pGEM vector (Promega) was used for in vitro transcription/translation of abi-2, c-ab1, and their respective deletion mutants. The entire abi-2 coding sequence was subcloned into the pGEM vector at the Bam H1 site. This plasmid, designated pGEM/abi-2, was subsequently digested with Stu 1 to remove the sequence encoding amino acids 244–401 from abi-2 and ligated to generate pGEM/abi-2Δ244-401. To generate the SH3 domain deletion of Abi-2, the DNA sequence encoding amino acids 161–321 of Abi-2 was amplified by Polymerase Chain Reaction (PCR). The following forward and reverse oligonucleotide primers were used for PCR amplification: 5'-GTTGCAAGAAGAGAAAT-3' (SEQ ID NO:1) and 5'-GAAGATCTGGAGCCCACGGT-3' (SEQ ID NO:2). A termination codon and restriction sites for Bam H1 Eco R1, and Hind III were engineered at the 3' of the PCR product to facilitate subcloning and to ensure appropriate termination of translation. The PCR-generated cDNA fragment was digested with Kpn 1/Hind III and subcloned into pGEM/abi-2 at the Kpn 1 and Hind III sites. The resultant plasmid was designated pGEM/abi-2ΔSH3.

To express abi-2 in mammalian cells, a modified pCGN expression vector (Tanaka and Herr, Cell 60:375–386 (1990)) was used. The entire coding sequence of abi-2 was subcloned in frame into pCGN at Bam H1 site downstream of the sequence encoding the HA tag. The resultant plasmid pCGN/abi-2, under the control of the CMV promoter, directs the synthesis of Abi-2 with an HA tag fused at its N-terminus.

Construction of pCGN/abi-2Δ1-100 was performed by cutting the pGEM/abi-2 plasmid with Xba 1, filling in with Klenow, and adding a Bam H1 linker to the 5' end of abi-2. The cDNA fragment with a 5' deletion was then subcloned in frame into the pCGN vector. To create pCGN/abi-2Δ1-157, the pGEM/abi-2 plasmid was cut with Kpn 1, blunted at the 5' end, and following addition of a Bam H1 linker at the 5', the Bam H1 cDNA fragment of abi-2 was subcloned into pCGN. The plasmid pCGN/abi-2Δ158-243 was created by an internal deletion of pGEM/abi-2 at the Kpn 1 and Stu1 sites. The abi-2 DNA fragment containing the internal deletion was then subcloned into pCGN.

pCGN/c-ab1 and pGEM/ab1ΔSH3 were constructed as described previously (Pendergast et al, Proc. Natl. Acad. Sci. USA 88:5927 (1991)). To generate C-terminal deletion mutants of c-Ab1, a PCR-directed mutagenesis strategy was employed as described (Dai et al., J. Biol. Chem. 267:19565 (1992)). The resultant plasmids, designated pGEM/ab1ΔSH3Δ544-601 and pGEM/ab1SH3Δ544-637, respectively, bear double deletion of sequences encoding both SH3 and C-terminal amino acids as indicated.

The pGEX 3x vector (Pharmacia) was used to express a GST-Abi-2 fusion protein. The entire coding sequence of abi-2 was subcloned in frame into pGEX-3x at the Bam H1 site and the plasmid created was designated pGEX/abi-2. cDNA fragments encoding the SH3 and SH2 domains of c-Ab1 were subcloned in frame into pGEX 3x as described (Pendergast et al, Cell 66:161 (1991)). cDNA fragments encoding Ab1 C-terminal amino acids 593–1149, 593–730, and 731–1149 were excised from pGEM/c-ab1 by appropriate restriction enzyme-digestions and subcloned in frame into pGEX 3x. These DNA fragments of c-ab1, together with the full length c-ab1 and c-ab1ΔSH3, were also subcloned in frame into pAS-CYH2 (obtained from S. Elledge) (Harper et al, Cell 75:805 (1993)) for testing the interaction by the yeast two-hybrid system.

Yeast Two-Hybrid Screen

The yeast two-hybrid system was employed to screen a human lymphocyte cDNA library as described by Durfee et al, Genes Dev. 7:555 (1993)). The bait plasmid of cPC60/ab1SH3 was cotransformed with the cDNA library into yeast strain Y190 (Harper et al, Cell 75:805 (1993)). $4 \times 10^5$ transformants were screened for lac Z reporter gene expression by a filter lift assay (Durfee et al, Genes Dev. 7:555 (1993)). The colonies that turned blue in 4 hours were replicated onto a minus trytophan, leucine and histidine plate containing 25 mM-3-AT and grown at 30° C. for 3 days. Total DNA was isolated from the colonies grown and used to transform the DH5α bacterial strain by electroporation using a Bio-Rad GenePulser. Plasmid DNA was isolated from Ampicillin resistant colonies and tested for bait-dependent reporter gene expression by retransforming back into yeast strain Y190 with pAS-CYH plasmid alone or bait plasmid pPC60/ab1SH3. cDNAs that provided bait-dependent lac Z gene activation were subcloned into pBSK and subjected to dideoxy chain termination sequencing. Sequence analysis was performed with the Genetics Computer Group program (Pearson and Lipman, Proc. Natl. Acad. Sci. USA 85:2444 (1988)). FASTA searches for homologous sequences were performed against the SwissProt, PirProtein, and GenBank data libraries.

PCR amplification of abi-2 5' untranslated sequence was performed using the human lymphocyte cDNA library as template. The forward and reverse oligonucleotide primers used are: 5'-TGATGAAGATACCCCACCA-3' (SEQ ID NO:3) and 5' CTGGTCGTTCAAGGTTGGCTGGAGC-3' (SEQ ID NO:4). Amplified cDNA fragments were purified by agarose gel electrophoresis and subcloned into pBSK. Plasmid DNA from three independent colonies were prepared and sequenced. All three colonies contain cDNA inserts that represents the 5' untranslated sequence of ab1-2.

Subcellular Fractionation

Subcellular fractionation was performed as described (Dignam et al, Nucl. Acids Res. 11:1475 (1983)). Approximately $2 \times 10^7$ RAMOS cells were washed once with PBS and once with hypotonic buffer (10 mM HEPES, pH7.9; 1.5 mM MgCl$_2$, 10 mM KCl, 0.2 mM PMSF, 0.5 mM DTT, 5 mg/ml leupeptin). Cells were swollen in a 3-fold packed cell volume of hypotonic buffer for 10 min, and homogenized by passing through a $27^{1/2}$ G needle 5–10 times. Release of cytosol was checked under the phase microscope. Cell lysates centrifuged at 3300 g for 15 min to separate the nuclei from the cytosol/membrane fraction.

A second procedure, as described by Sakai et al, EMBO J. 13:3748 (1994) was also used with minor modifications. Approximately $2 \times 10^7$ RAMOS cells were homogenized in 1 ml of hypotonic suspension buffer (20mM Tris, pH7.5 1 mM EDTA, 1 mM EGTA DTT, 1 mM PMSF and 1 mM Na$_3$VO$_4$) by passing through a $27^{1/2}$ G needle 5 times, followed by centrifugation at 1000 g for 15 min. The nuclear pellet and the supernatant containing cytosol and membrane fractions were suspended in equal volumes of 2×SB and subjected to SDS-PAGE analysis. Isolation of chromatin was performed as described (Hancock et al, Methods Cell. Biol. 15:127 (1977)).

Expression and Purification of GST-Fusion Proteins

GST fusion protein expression was induced as described (Pendergast et al, Proc. Natl. Acad. Sci. USA 88:5927 (1991)). The fusion proteins were purified on glutathione-Sepharose 4B (Pharmacia) beads as previously described (Pendergast et al, Cell 66:161 (1991)).

In vitro Transcription and Translation

In vitro transcription/translation was performed using the SP6 in vitro transcription/translation kit (Promega) according to manufacturer's specifications. The reaction was incubated at 30° C. for 2 hr and in vitro translated protein products were directly analyzed by SDS-PAGE or subjected to immunoprecipitation/binding assay prior to SDS-PAGE as indicated.

Binding Assays

Radiolabeled proteins from whole-cell lysates or translated in vitro in reticulocyte lysates were diluted 5-fold with incubation buffer (20 mM HEPES, pH7.0, 150 mM NaCl, 0.1% Triton X-100, 10% glycerol, 0.5 mM $Na_3VO_4$, 0.1 mM $Na_2MoO_4$, 20 mM NaF, 1 mM PMSF, 25 mg/ml leupeptin) and incubated with GST or GST fusion proteins attached to glutathione-Sepharose beads. After incubation for 90 min at 4° C., the beads were washed four times with same buffer unless otherwise indicated. The beads were boiled in 2× sample buffer and bound proteins were analyzed by SDS-PAGE.

Immunoblotting

Proteins were separated on SDS-PAGE and transferred to nitrocellulose filters. Immunoblotting was performed as described previously (Pendergast et al, Cell 75:175 (1993)). Immunoreactive proteins were visualized by the enhanced chemiluminescence (ECL) detection system (Amersham) according to manufacturer's specifications.

In vitro Kinase Assay

In vitro kinase assay was performed as described (Konopka et al, Cell 37:1035–1042 (1985)). Phosphorylaton was carried out in the presence of $[\gamma-^{32}P]$ ATP and $MnCl_2$ for 30 min at 30° C.

Retrovirus Infections

Helper-free retroviral stocks were prepared by transient hyperexpression in Bosc 23 cells as previously described (Muller et al, Mol. Cell. Bio. 11:1785 (1991); Pear et al, Proc. Natl. Acad. Sci. USA 90:8392 (1993)). Infection of NIH-3T3 fibroblasts with the indicated retroviruses was performed using polybrene as previously described (Muller et al, Mol. Cell. Bio. 11:1785 (1991)). Following a 4 hr infection period, the cells were placed in fresh medium (DMEM+10% FCS) and cultured for 2½ days before selection with G418. Cells were selected for 22 days. Western blot analysis was performed on cell populations at 2½ days post-infection and after 22 days of G418 selection. Cell transformation was quantitated by growth in soft agar as described previously (Muller et al, Mol. Cell. Biol. 11:1785 (1991)). The cells ($1 \times 10^4$) were plated per 6-cm dish in duplicate. Agar colonies with a diameter of >0.5 mm were counted ~2 weeks after plating the cells.

Example I

Cloning of an Abl Interacting Protein by the Yeast Two-Hybrid System

To identify proteins that interact with the Abl regulatory domains, the yeast two-hybrid system was employed (Fields and Song, Nature 340:245–246 (1989)). A human lymphocyte library was screened as genetic and biological data suggest that c-Abl plays a role in lymphocyte development (Schwartzberg et al, Cell 65:1165 (1991); Tybulewicz et al, Cell 65:1153 (1991); Caracciolo et al, Science 245:1107 (1989)). Using the Abl SH3 domain as a bait, 24 positive clones were identified out of $4 \times 10^5$ transformants. Among these, clone AS3B2 was demonstrated to confer a bait plasmid-dependent expression of lac Z in yeast strain Y190 and grew in his⁻, trp⁻, leu⁻ selection plates with 25 mM 3-aminotriazole (3-AT). Nucleotide sequence analysis revealed that AS3B2 contains a single long open reading frame (ORF). The complete coding sequence of AS3B2 encompasses 1203 nucleotides. The gene contained in AS3B2 was designated abi-2 for Abl Interacting protein 1 (Aip-1) (Feller et al, Trends Biochem. Sci. 19:453–458 (1994)). The amino acid sequence of Abi-2 is shown in FIG. 1,A and the nucleotide sequence of abi-2 is shown in FIG. 2.

Interestingly, the basic, N-terminal region of Abi-2 exhibits 40 to 50% similarity over a 53-amino acid stretch to the DNA-binding region of homeodomain proteins (FIGS. 1, A, and C) (Rushlow et al, Genes Dev. 1:1268 (1987); Scott et al, Biochem. Biophys. Acta 989:25 (1989); Pabo and Sauer, Annu. Rev. Biochem. 61:1053 (1992)). Homeodomain proteins have been implicated in specifying positional information in the embryo during development and in the control of cell lineages by regulating the expression of cell type-specific genes (Scott et al, Biochem. Biophys. Acta 989:25 (1989)). It is significant that all of the amino acids in the homeodomain that are implicated in contacting the DNA major groove are conserved in the basic region of Abi-2. Similarly, all of the amino acids that contact the DNA backbone with the exception of an invariant tryptophan, are present in this domain of Abi-2 (FIG. 1C) (Pabo and Sauer, Annu. Rev. Biochem. 61:1053 (1992)).

Search of the database for homologous sequences revealed that the abi-2 DNA sequence is 70% identical to that of the *Xenopus laevis* xlan 4 DNA (Redy et al, Mech. Dev. 39:143 (1992)). The predicted amino acid sequence of the Xlan 4 protein is 93% identical to that of the last 286 amino acids of Abi-2. Remarkable conservation of the SH3 domain, PEST sequences, serine-rich region, proline-rich stretches and phosphorylation sites is observed among the human Abi-2 and predicted Xenopus Xlan 4 proteins. The xlan 4 gene is expressed as a maternal transcript and localizes in the animal pole region of the oocyte. The expression of xlan 4 is developmentally regulated (Redy et al, Mech. Dev. 39:143 (1992)). More recently, a mouse gene with high homology to the human abi-2 was cloned as cDNA encoding an Abl-binding protein. The corresponding protein was designated Ahl interactor 1 (Abi-1) and its predicted amino acid sequence is 65% identical to that of Abi-2.

Example II

Expression of Abi-2 in Human Tissues

To investigate the expression pattern of abi-2, Northern blot analysis was performed on poly A selected RNA from multiple human tissues. Using the abi-2 cDNA as a probe, two transcripts, sized at 7 Kb and 1.9 Kb respectively, were detected in all tissues examined (FIG. 1D). The abundance of the two transcripts varies among tissues. The expression of the 7 Kb transcript appears constant in most tissues examined with the exception of colon and peripheral blood leukocytes where low levels of the transcript are detected. Although detectable in almost all tissues examined, 1.9 Kb transcript is relatively abundant in testes, ovary, thymus, and colon with lower but detectable levels in prostate, peripheral blood leukocytes and spleen. It is most likely that abi-2 corresponds to the 1.9 kb transcript. The 7 Kb transcript may be the product of a related gene or an alternative spliced form of the abi-2 gene.

Example III

Expression of the Abi-2 Protein

The complete coding sequence of abi-2 was subcloned into the pGEM vector downstream of the SP6 promoter and the resulting construct was then used for in vitro transcription/translation. Analysis of the in vitro transcription/translation products by SDS-PAGE revealed the presence of three major protein bands with apparent molecular weights of 75-, 55-, and 40-KDa (FIG. 3A, lane 3). All three proteins were recognized by antibodies to Abi-2 (FIG. 3a, lane 5) but not by the corresponding pre-immune serum (FIG. 3A, lane 4). The two lower sized proteins (55- and 40-KDa) may represent products from an internal initiation site or proteolytic degradation fragments. Several potential translational initiation sites are found in the abi-2 nucleotide sequence. Using the first ATG as the initiation codon, the calculated molecular weight of Abi-2 is 44-Kda. Aberrant protein migration has been reported for several proteins which, like Abi-2, are proline-rich and contain stretches of basic/acidic amino acids (Matthews et al, Mol. Cell. Biol. 12:2396 (1992)).

The expression of Abi-2 was next investigated in human Bosc 23 cells (Pear et al, Proc. Natl. Acad. Sci. USA 90:8392 (1993)) following transfection of abi-2 cloned in a mammalian expression vector under the control of the CMV promoter (Tanaka and Herr, 60:375 (1990)). A sequence coding for the influenza virus hemagglutinin epitope (HA) was fused in frame at the 5' end of the abi-2 sequence for detection of the gene product with monoclonal antibody (12CA5) against the HA-tag. The construct directs production of two broad protein bands of approximately 75- and 55-KDa in the Bosc 23 human embryonic kidney cells. The two proteins were recognized in Western blot analysis with monoclonal antibody to the HA epitope tag (FIG. 3B, lane 2) as well as polyclonal antibodies to Abi-2 (FIG. 3B, lane 3). Expression of endogenous Abi-2 protein was investigated using the human B lymphoid cell line, RAMOS. Western blot analysis with antibodies to Abi-2 revealed two proteins with apparent molecular weights of 75- and 55-KDa (FIG. 3B, lane 4). The two proteins co-migrated with the proteins expressed in Bosc 23 cells following transfection with the abi-2 cDNA (FIG. 3B, lane 3).

Example IV

Subcellular Localization of Abi-2

The subcellular localization of Abi-2 was determined by cellular fractionation employing two distinct procedures (Dignam et al, 11:1475 (1983); Sakai et al, EMBO J. 13:3748 (1994)). Endogenous Abi-2 protein from RAMOS cells was shown to be localized primarily in the nucleus, with lower but significant levels in the cytosol and membrane fractions (FIG. 3C). Interestingly, the nuclear Abi-2 protein was mostly full length (75 KDa), while equal amounts of the 75 KDa and 55 KDa forms of Abi-2 were present in the cytoplasm (FIG. 3C, lanes 2 and 3). These results suggest that the nuclear pool of Abi-2 may not be accessible to the activity of specific proteolytic enzymes present in the cytoplasm or alternatively, that Abi-2 is protected from degradation in the nucleus by formation of specific protein complexes. The nuclear Abi-2 protein appears to be associated with chromatin. Significantly, the subcellular distribution of Abi-2 is similar to that of c-Abl (Van Etten et al, Cell 58:669 (1989); Van Etten et al, J. Cell. Biol. 124:325 (1994); Wetzler et al, J. Clin. Invest. 92:1925 (1993)).

Example V

Abi-2 binds to c-Abl In Vitro and In Vivo

It has been shown that Abi-2 binds to the Abl SH3 domain in yeast. To determine whether Abi-2 can interact with the full length c-Abl protein, a GST-Abi-2 fusion protein was used in an in vitro binding assay with full length c-Abl produced in baculovirus-infected insect cells (Pendergast et al, Cell 75:175 (1993)). As shown in FIG. 4A, the GST-Abi-2 protein interacts with full length c-Abl in solution. The binding of Abi-2 to c-Abl appears to be selective as shown by the failure of Abi-2 to form a complex with another SH3-containing protein, the guanosine triphosphatase-activating protein (GAP) of Ras (FIG. 4A, lanes 4–6) (Trahey et al, Science 242:1697 (1988)).

To examine the interaction of Abi-2 with c-Abl in vivo antibodies were developed to the Abi-2 protein. Interestingly, analysis of the Abi-2 protein by SDS-PAGE revealed that Abi-2 migrates aberrantly. While the calculated molecular weight of the protein encoded by the abi-2 cDNA is 44 kDa, the Abi-2 protein produced in bacteria or translated in vitro in a reticulocyte lysate migrates with an apparent molecular weight of 55 kDa (FIG. 6B). In addition to the major 55 kDa band, two proteins of 44 kDa and 75 kDa are obtained following in vitro transcription/translation using the abi-2 cDNA which are recognized by an anti-Abi-2 polyclonal antibody raised against full length Abi-2. The smaller 44 kDa protein is likely to be produced by translation from an internal initiation codon because it cannot be recognized by antibodies specific to the Abi-2 N terminus. The 75 kDa protein may result from additional post translational modifications. A 75 kDa protein is the predominant product obtained following transfection of the abi-2 cDNA in Bosc23 human embryonic kidney cell (FIGS. 4B and C). The 75 kDa protein is recognized by anti-Abi-2 antibodies. The 75 kDa protein and a minor 55 kDa protein are also detected with the anti-Abi-2 polyclonal antibodies in lysates from human B lymphoid cells.

Interaction of Abi-2 with c-Abl in vivo was examined following overexpression of wild type c-Abl and Abi-2 in human Bosc 23 cells and immunoprecipitation with antisera to Abi-2 or c-Abl. Bosc 23 cells were transfected with pCGN/abi-2 and pSRα/c-abl mammalian expression plasmids. After 2½ days, the cells were lysed and the lysates were incubated with anti-Abl, anti-Abi-2 or pre-immune sera. The immunoprecipitates were then subjected to in vitro kinase assays with [$\gamma^{32}$-P] ATP to radiolabel the proteins. A 145 kDA protein was precipitated by the anti-Abi-2 antibody but not the corresponding pre-immune sera (FIG. 4B, lanes 1 and 2). This 145 kDA protein comigrated with a protein of the same size which was immunoprecipitated with anti-Abl antibodies from the same cells (FIG. 4B, lane 3). The identity of the 145 kDA protein as c-Abl was confirmed by subjecting the precipitated proteins to a second round of immunoprecipitation with anti-Abl antibodies. A 145 kDA protein immunoreactive with anti-Abl antibodies is observed following incubation of a portion of the samples corresponding to lanes 2 and 3 in FIG. 4B with anti-Abl antibodies (FIG. 4C). Thus, the c-Abl wild type protein is precipitated with antibodies to Abi-2 as detected by its in vitro autophosphorylation activity.

A radiolabeled protein of approximately 75 kDA was detected in both anti-Abi-2 and anti-Abl immunoprecipitates from lysates of Bosc 23 cells co-transfected with the pCGN/abi-2 and pSRα/c-abl expression plasmids (FIG. 4B, lanes 2 and 3). To examine whether this protein was Abi-2, a portion of the immunoprecipitates was boiled in the presence of SDS to denature the proteins and disrupt protein/protein interactions, diluted with buffer lacking SDS and then incubated with anti-Abi-2 antibodies or the corresponding pre-immune sera. A 75 kDA protein was precipitated with anti-Abi-2 but not the pre-immune sera from both, the anti-Abi-2 and anti-Abl immunoprecipitates of the Bosc 23 cell lysates (FIG. 4C, lanes 1, 2, 4 and 5). These results show that full length Abi-2 interacts with c-Abl following overexpression of both proteins in Bosc 23 cells and that Abi-2 becomes phosphorylated in an in vitro kinase assay in the presence of the c-Abl tyrosine kinase.

It has also been observed that endogenous Abi-2 co-immunoprecipitates with the endogenous c-Abl protein in B cell lysates. However, the reciprocal co-precipitation of c-Abl with anti-Abi-2 antibodies has not been shown in lysates from these cells. The inability of the anti-Abi-2 antibodies to co-precipitate endogenous c-Abl in B cells may result from association of the Abi-2/c-Abl complex with other proteins in the B cell lysates that mask the antigenic epitopes recognized by the anti-Abi-2 antibodies. Alternatively, the phosphorylation state of the c-Abl and Abi-2 proteins in the complex may result in differential recognition of the complexed Abi-2 protein by the corresponding antibodies. It has been shown that, unlike endogenous c-Abl, the overexpressed c-Abl protein is tyrosine phosphorylated and activated (Pendergast et al, Proc. Natl. Acad. Sci. USA 88:5927 (1991)). The overexpressed and activated c-Abl kinase may phosphorylate Abi-2 in the Bosc 23 cells allowing the appropriate antigenic sequences to become accessible to the anti-Abi-2 antibody.

Example VI

Abi-2 Binds to Multiple Surfaces on the c-Abl Protein

Figure 5D:
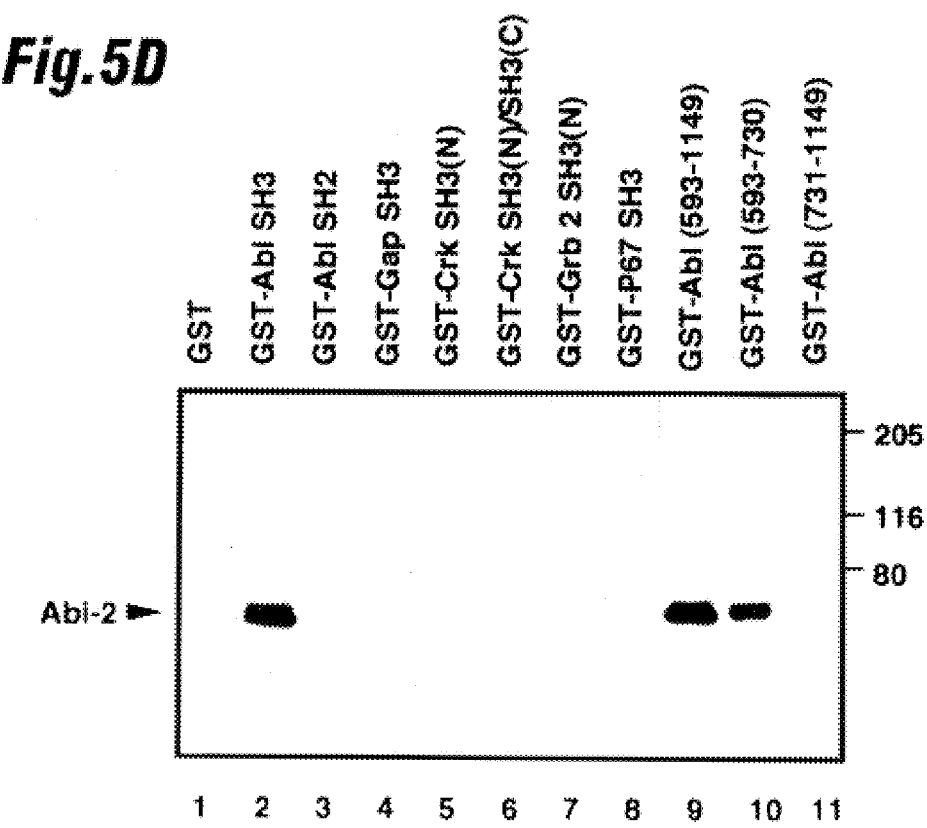
Figure 5A:
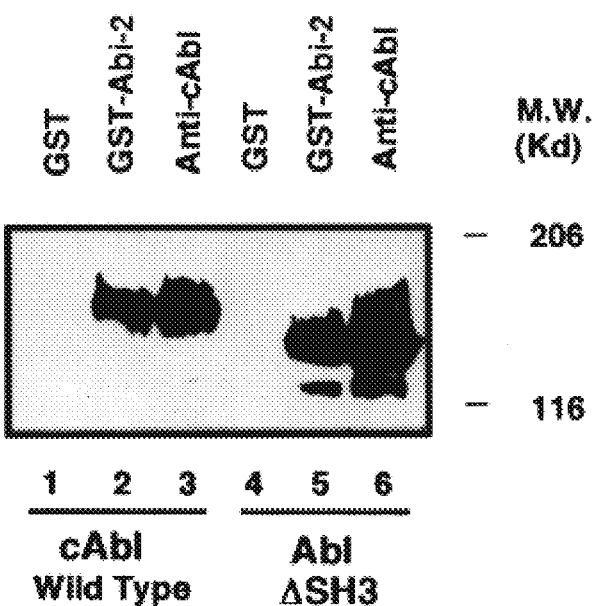

To confirm that the Abl SH3 domain was responsible for the interaction between c-Abl and Abi-2, a mutant c-Abl protein lacking the SH3 domain was examined to determine whether it was deficient in binding to Abi-2. Surprisingly, the c-AblΔSH3 mutant bound to Abi-2 as efficiently as wild type c-Abl (FIG. 5A). This result suggested that, in addition to the SH3 domain, other-sequences in c-Abl may participate in binding to Abi-2. Using both the yeast two-hybrid system and in vitro binding assays, a second region in the C-terminus of c-Abl was identified that interacted strongly with Abi-2 (FIG. 5B and FIG. 5D, lanes 9 and 10). The Abi-2-binding region in the C-terminus of c-Abl maps to sequences near the nuclear localization signal. Recently, it was reported that this region of c-Abl can bind to the SH3-containing Crk, Grb2 and Nck adaptor proteins (Ren et al, Genes Dev. 8:783 (1994)). Three distinct proline-rich binding sites for the adaptor proteins were found within this region of c-Abl. The presence of an SH3 domain in Abi-2 suggested that Abi-2 may also interact with c-Abl by direct binding of the Abi-2 SH3 domain with the proline-rich sequences in the C-terminus of c-Abl.

Figure 5C:
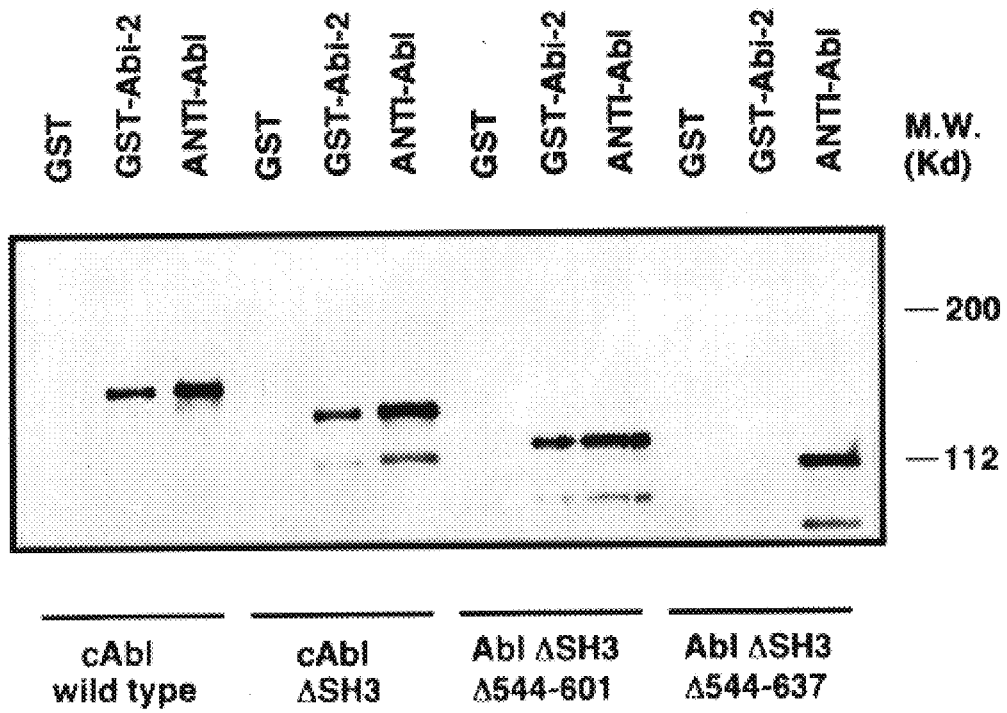
Figure 5B:
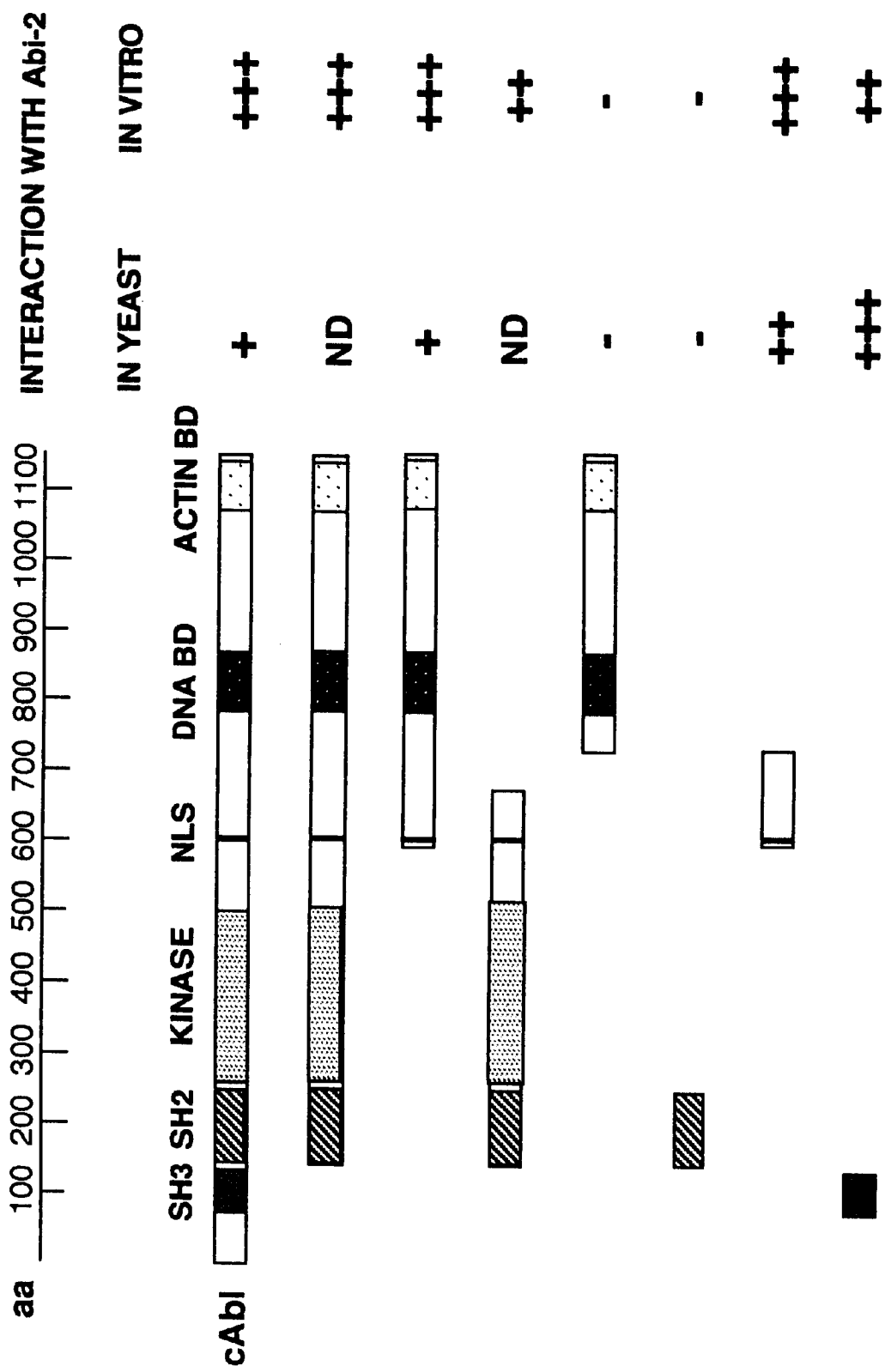

To more precisely define the Abi-2 binding site in the Abl C-terminus, additional c-Abl mutants were created and tested for binding to Abi-2 (FIG. 5C). Two of the three proline rich stretches identified in c-Abl that bind to SH3 domains are found upstream of the nuclear localization sequence, while the third proline stretch is downstream of this sequence (Ren et al, Genes Dev. 8:783 (1994)). Deletion of the two proline-rich sites upstream of the nuclear localization signal (Δ544-601) did not diminish binding of c-AblΔSH3 to Abi-2 (FIG. 5C, lane 8). In contrast, deletion of additional sequences including the third proline-rich site (Δ544-637), completely abolished binding of c-AblΔSH3 to Abi-2 (FIG. 5C, lane 11). These results indicate that Abi-2 binds to c-Abl by interacting directly with the Abl SH3 domain and a proline-rich stretch downstream of the nuclear localization signal in the Abl C-terminus.

Example VII

Specificity of Binding of Abi-2 to the Abl SH3 Domain

Specificity in the interaction of the various SH3 domains with their proline-rich targets is necessary for the proper transmission of intracellular signals involving distinct signal transduction pathways and protein regulatory cascades (Pawson, Nature 373:573 (1995); Cohen et al, Cell 80:237 (1995)). To determine whether the interaction between the Abl SH3 domain and Abi-2 is selective, a number of SH3 domains from distinct proteins were compared for their ability to bind to Abi-2. No interactions were detected between Abi-2 and the SH3 domains of GAP, Crk (N-terminal), Crk (N-terminal and C-terminal), Grb2 (N-terminal), and the p67 protein from neutrophils (FIG. 5D, lanes 4 to 8). Also, no interaction was detected between Abi-2 and the SH3 domain of the Src protein tyrosine kinase. These results indicate that the interaction between Abi-2 and the Abl SH3 domain is highly specific and that Abi-2 contacts a second region in the C-terminus of c-Abl with high affinity.

Example VIII

Binding of c-Abl to the Proline-Rich N-Terminus and C-Terminal SH3 Domain of Abi-2

To map the sites on Abi-2 that interact with c-Abl, a series of Abi-2 deletion mutants was generated (FIG. 6A) and tested for binding to GST-fusion proteins containing the Abl SH3 domain and Abl C-terminal sequences (FIGS. 6B and 6C). Wild type (full length) and C-terminal truncated Abi-2 proteins were synthesized by in vitro transcription/translation in a rabbit reticulocyte lysate. The predominant in vitro transcription/translation products generated from the full length abi-2 cDNA migrate with apparent molecular weights of 55 and 44 kDA (FIG. 6B). Deletion of the Abi-2 SH3 domain abrogates binding to the proline-rich Abl C-terminal sequences encompassing amino acids 593 to 730 (FIG. 6B, lane 6). Further deletion of sequences upstream of the Abi-2 SH3 domain that contain a polyproline stretch and a PEST domain does not affect binding to the Abl SH3 domain (FIG. 6B, lane 8).

To identify the proline-rich sequences in Abi-2 that mediate its binding to the Abl SH3 domain, Abi-2 mutant proteins were generated containing deletions of proline-rich sequences localized in the N-terminal or central regions of the protein (FIGS. 6A and 6C). The Abi-2 proteins were produced in mammalian COS cells and tested for binding to Abl sequences. As shown in FIG. 6C, deletion of the most N-terminal proline-rich stretch of Abi-2 eliminates binding to the Abl SH3 domain (FIG. 6C, lane 5). This 10-amino acid proline-rich stretch exhibits strong similarity to the Abl SH3-binding site in 3BP-1 (Cohen et al, Cell 80:237 (1995)). Thus, the results show that the c-Abl tyrosine kinase contacts Abi-2 at two sites: an N-terminal proline-rich stretch and the Abi-2 SH3 domain. A model for the interaction between c-Abl and Abi-2 is shown in FIG. 8D.

Example IX

Abi-2 is a Substrate for the c-Abl Tyrosine Kinase In Vitro and In Vivo

The strong association between Abi-2 and c-Abl suggested that Abi-2 may be a target for tyrosine kinase activity of c-Abl. Additional support for this suggestion was provided by the observation that Abi-2 became phosphorylated in immune complex in vitro kinase assays following co-precipitation with the c-Ab1 tyrosine kinase from Bosc 23 cell lysates co-expressing the two proteins (FIGS. 4B and C). To determine whether c-Ab1 can phosphorylate purified Abi-2 protein, wild type and kinase defective forms of c-Ab1 were synthesized by in vitro transcription/translation in a reticulocyte lysate (FIG. 7A) and tested for their ability to phosphorylate purified GST or GST-Abi-2 proteins in vitro. Abi-2 was phosphorylated to high levels by wild type but not kinase defective c-Ab1 (FIG. 7A). A c-Ab1 mutant protein, c-Ab1ΔSH3Δ544-637 that retains tyrosine kinase activity but is defective in binding to Abi-2 (FIG. 5C), did not phosphorylate Abi-2 in this assay (FIG. 7A, lane 6).

It was then determined whether Abi-2 could be phosphorylated in vivo by c-Ab1 following expression in Bosc 23 cells. The cells were cotransfected with pCGN/abi-2 and pSRα/c-ab1 plasmids. Two days post-transfection, the cells were lysed and the lysates subjected to western blot analysis with anti-phosphotyrosine antibodies. Western blotting with anti-Ab1 and anti-HA antibodies was also performed to detect the expression of c-Ab1 and the HA-tagged Abi-2, respectively (FIG. 7B). Coexpression of Abi-2 with wild type c-Ab1 resulted in a marked increase in Abi-2 tyrosine phosphorylation (FIG. 7B, lane 4). These data show that Abi-2 can be phosphorylated by the activated c-Ab1 tyrosine kinase in vivo.

Example X

Expression of an Abi-2 Mutant Protein Uncovers the Transforming Activity of c-Ab1

The findings that Abi-2 binds to c-Ab1 via dual SH3 domain/proline-rich sequence interactions and that Abi-2 is a substrate of the c-Ab1 tyrosine kinase strongly suggested that Abi-2 modulates the biological properties of c-Ab1 in the cell. Two biological assays are available to examine the effects of Ab1 expression in vivo. First, overexpression of c-Ab1 wild type in NIH-3T3 cells has been shown to elicit growth arrest and result in counterselection of the expression of the c-Ab1 protein (Jackson et al, EMBO J. 12:2809 (1993); Sawyers et al, Cell 77:121 (1994)). Second, specific alterations in the c-Ab1 structure have been shown to result in cell transformation (Wang, Curr. Opin. Genet. Dev. 3:35 (1993). To examine whether Abi-2 can affect the biological properties of c-Ab1, NIH-3T3 cells were transfected with hygromycin-containing mammalian expression vectors encoding full length or truncated forms of Abi-2. Expression of full length Abi-2 could not be detected following transfection and hygromycin drug selection. Like the Ab1 proteins, full length Abi-2 appears to exert cytotoxic, and possibly cytostatic, effects on cells following overexpression (Ziegler et al, Cell 27:477 (1981); Renshaw et al, EMBO J. 11:3941 (1992); Jackson et al, EMBO J. 12:2809 (1993); Sawyers et al, Cell 77:121 (1994)). In contrast, an N-terminal truncated form of Abi-2 lacking the homeodomain homologous region and the proline-rich sequences required for interaction with the Ab1 SH3 domain (Abi-2Δ1-157) was readily expressed in NIH-3T3 cells (FIG. 8A). Cells expressing the Abi-2Δ1-157 mutant and cells expressing the vector alone were infected with retroviruses encoding wild type c-Ab1 or a kinase-defective form of c-Ab1, c-Ab1 K290R (FIG. 8B). A fraction of the cells was collected at 2½ days post-infection, lysed and subjected to western blot analysis with anti-Ab1 antibodies. Similar levels of c-Ab1 wild type and c-Ab1 K290R proteins were detected in control NIH-3T3 cells and in NIH-3T3 that stably expressed the Abi-2Δ1-157 mutant (FIG. 8B, upper left panel). Surprisingly, analysis of drug-selected cells at 22 days post-infection revealed that while the c-Ab1 wild type protein was counter selected in control NIH-3T3 cells in accordance with previous observations (Sawyers et al, Cell 77:121 (1994)), c-Ab1 was expressed to high levels in NIH-3T3 cells that co-expressed the Abi-2Δ1-157 mutant protein (FIG. 8B, lower left panel). As shown previously, the kinase-defective c-Ab1 K290R protein was not counter selected in NIH-3T3 cells, and similar levels of this protein were detected in control and Abi-2Δ1-157-expressing cells following drug selection at 22 days post-infection (FIG. 8B, lower left panel). To determine whether co-expression of the truncated form of Abi-2 and c-Ab1 wild type resulted in activation of the tyrosine kinase activity of c-Ab1, the lysates were subjected to western blot analysis with antiphosphotyrosine antibodies. As shown in FIG. 8B, right panel, expression of Abi-2Δ1-157 activates the tyrosine kinase activity of c-Ab1 in NIH-3T3 cells. No enhanced tyrosine phosphorylation is detected in cells co-expressing Abi-2Δ1-157 and a kinase defective form of c-Ab1 (FIG. 8B, right panel).

Figure 8C:
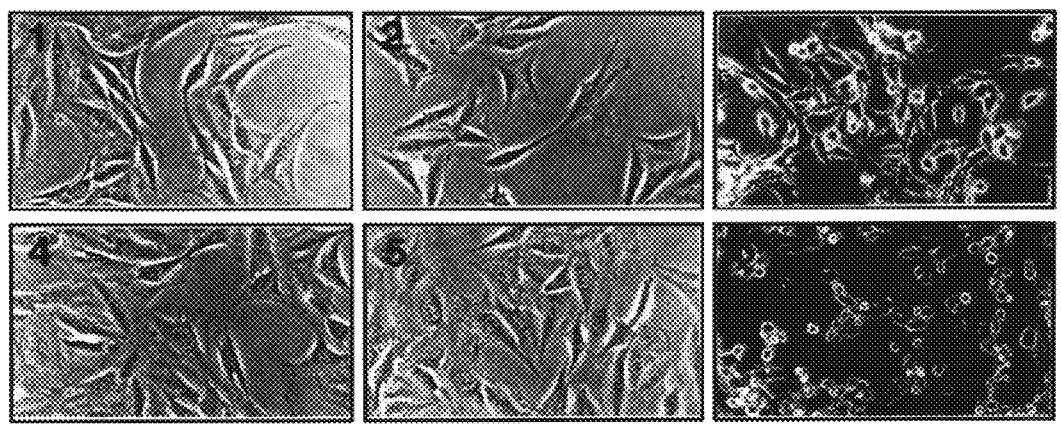
Figure 8D:
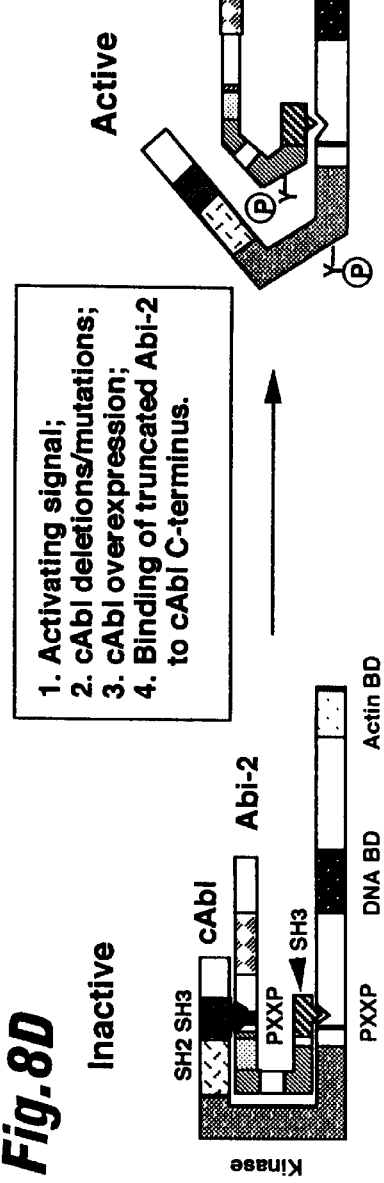

A striking difference was observed among the cells co-expressing c-Ab1 wild type and Abi-2Δ1-157 and those cells expressing Abi-2Δ1-157 alone, c-Ab1 alone, vector control, or co-expressing Abi-2Δ1-157 and a kinase-defective form of c-Ab1 (FIG. 8C). Cells that co-expressed Abi-2Δ1-157 and c-Ab1 wild type were morphologically transformed and exhibited a similar morphology to those NIH-3T3 cells expressing the v-ab1 oncoprotein (FIG. 8C, panels 3 and 6). To directly examine whether the cells co-expressing Abi-2Δ1-157 and cAb1 wild type were transformed, colony formation in soft agar was assayed as a measure of anchorage-independent growth (Muller et al, Mol. Cell. Biol. 11:1785 (1991)). As shown in Table 1, cells co-expressing the Abi-2Δ1-157 mutant and cAb1 wild type exhibit a dramatic increase in soft agar plating efficiency compared to cells expressing either protein alone or to cells expressing both the Abi-2Δ1-157 mutant and a kinase defective form of cAb1. These results demonstrate that expression of the Abi-2Δ1-157 mutant protein activates the tyrosine kinase and transforming activities of c-Ab1 in NIH-3T3 cells.

TABLE 1

Transformation of NIH 3T3 cells by co-expression of c-AbI and a truncated Abi-2 protein

| | No. of Agar Colonies[c] | |
|---|---|---|
| Retroviruses[a] | NIH 3T3 vector[b] | NIH 3T3/Abi-2Δ1-157[b] |
| c-AbI wild type | 3 | 563 |
| c-AbI K290R | 2 | 3 |
| Tkneo | 4 | 3 |

[a]Helper-free retroviruses were prepared by transient overexpression in Bosc 23 cells.
[b]NIH 3T3 cells stably transfected with either pCGN vector alone or pCGN/abi-2Δ1-157 were infected with the indicated helper-free retroviruses. At 2 1/2 days post-infection the cells were selected with G418 and cultured for three weeks in the presence of the drug.
[c]Number of agar colonies per $10^4$ cells. The average frequency of colony formation in soft agar was determined from two plates per assay. Colonies with a diameter of >0.5 mm were counted approximately two weeks after plating the cells.

Example XI

Effect of Abi-2 Deletion Mutants on BCR/Ab1 Transforming Activity

To examine the effects of expressing various Abi-2 forms on the transforming activity of BCR-Ab1, Rat1 cell that stably expressed P185 BCR-Ab1 (Muller et al, Mol. Cell. Biol. 11:1785 (1991)) were employed. These cells are transformed as indicated by their ability to grow in soft agar. The Abi-2 proteins encoding sequences cloned in the pCGN - expression vector were introduced. As shown in FIGS. 9(A) and (B), the truncated Abi-2 proteins lacking N-terminal sequences were expressed to high levels following transient transfection in COS cells. Transfection of the truncated Abi-2 proteins in Rat1/P185 BCR-Ab1 cells, followed by drug (Hygromycin) selection, resulted in the stable expression of the truncated Δ1-100 and Δ1-157 Abi-2 proteins. In contrast, no clones expressing the full length Abi-2 protein were generated. The Rat1/BCR-Ab1 cells expressing the indicated proteins were then plated in soft agar. Agar colonies that grew after 3 weeks were counted.

As shown in FIG. 9(C) expression of the Abi-2 mutant protein, Abi-2Δ1-100, which lacks the N-terminal homeodomain homologous region but retains the two domains implicated in binding to the Ab1 SH3 domain and Ab1 C-terminal sequences, inhibits the transforming activity of the BCR/Ab1 oncoprotein by 70% in Rat1 cells. Interestingly, expression of the Abi-2 mutant, Abi-2Δ1-157, which lacks the sequences required for Ab1 SH3 domain binding while retaining binding to the C-terminal region of Ab1, does not inhibit BCR/Ab1-transforming activity and exerts a 2- to 3-fold stimulatory effect.

Example XII

Chromosomal Assignment of Abi-2

A mapping panel (No. 1) consisting of DNA from seventeen mouse-human and one Chinese hamster-human hybrids was obtained from NIGMS repository (Camden, N.J.). Characterization and human chromosome content are described in detail in the NIGMS catalog. DNA samples were digested with Bgl II, separated by electrophoresis on agarose gels, transferred to Hybond nylon filter (Amersham) and hybridized to the $^{32}$P-labeled cDNA probe as described (Yang-Feng et al, Am. J. Hum. Genet. 37:1117 (1985)). The cDNA identified seven human genomic fragments, 25, 12.5, 6.8, 6.1, 5.1, 4.2 and 3.3 kb, and detected six fragments, 16.5, 10.5, 7.6, 4.3, 3.9 and 3.2 kb, in the mouse DNA and five fragments, 6.6, 3.5, 3.2, 2.9, and 0.4 kb, in the hamster DNA. The 3.3 kb human fragment could not be clearly distinguished from the mouse or hamster 3.2 kb band, therefore, could not be scored for in hybrids. The results of discordancy analysis are summarized in FIG. 13. The Abi-2 sequence showed perfect segregation with human chromosome 2.

Regional mapping of Abi-2 was accomplished by in situ hybridization. The cDNA clone was nick-translated with {$^3$H} dCTP and {$^3$H} TTP to a specific activity of $2.5 \times 10^7$ cpm/μg and hybridized to human metaphase chromosomes at a concentration of 25 ng/ml. Of 138 grams over 50 cells analyzed, 20 (14.5%) were found to be at chromosome 2q33 and no other site was labeled above the background.

All documents cited above are hereby incorporated in their entirety by reference.

One skilled in the art will appreciate from a reading of this disclosure that various changes in form and detail can be made without departing from the true scope of the invention.

---

What is claimed is:

1. An isolated nucleic acid that consists of a nucleotide sequence that encodes a protein having the amino acid sequence given in SEQ ID NO:5, or a portion of said protein comprising 10 or more consecutive amino acids of the sequence given in SEQ ID NO:5.

2. The nucleic acid according to claim 1 wherein the protein has the amino acid sequence given in SEQ ID NO:5, or a portion thereof comprising 30 or more consecutive amino acids of the sequence given in SEQ ID NO:5.

3. The nucleic acid according to claim 1 wherein the protein has the sequence given in SEQ ID NO:5, or a portion thereof comprising 50 or more consecutive amino acids of the sequence given in SEQ ID NO:5.

4. The nucleic acid according to claim 1 wherein said portion comprises at least the SH3 domain of the sequence given in SEQ ID NO:5.

5. The nucleic acid according to claim 1 wherein said portion comprises at least the tyrosine phosphorylation site of the sequence given in SEQ ID NO:5.

6. A kit comprising the nucleic acid according to claim 1 disposed within a container means.

7. The nucleic acid according to claim 1 wherein said portion comprises at least a proline rich region of the sequence given in SEQ ID NO:5.

8. A recombinant molecule comprising said nucleic acid according to claim 1 and a vector.

9. The recombinant molecule according to claim 8 further comprising a promoter operably linked to said nucleic acid sequence.

10. A host cell comprising said recombinant molecule according to claim 8.

11. A method of producing a protein having the amino acid sequence given in SEQ ID NO:5, or a portion of said protein comprising 10 or more consecutive amino acids of the sequence given in SEQ ID NO:5, comprising culturing said host cell according to claim 10 under conditions such that said nucleic acid is expressed and said protein, or said portion thereof, is thereby produced, and isolating said protein or said portion thereof.

12. An isolated protein produced by the method according to claim 11.

13. An isolated nucleic acid that consists of a nucleotide sequence that encodes the amino acid sequence given in SEQ ID NO:5, or a portion of said protein comprising 100 or more consecutive amino acids of the sequence given in SEQ ID NO:5.

14. The nucleic acid according to claim 13 wherein the protein comprises the sequence given in SEQ ID NO:5, or a portion of said protein comprising 300 or more consecutive amino acids of the sequence given in SEQ ID NO:5.

15. An isolated nucleic acid that consists of a nucleotide sequence that encodes the amino acid sequence given in SEQ ID NO:5, or a portion of said protein comprising at least the homeodomain homologous region of the sequence given in SEQ ID NO:5.

16. An isolated nucleic acid that consists of a nucleotide sequence that encodes the amino acid sequence given in SEQ ID NO:5, or a portion of said protein that comprises at least amino acid residues 101 to 401 of the sequence given in SEQ ID NO:5.

17. An isolated nucleic acid that consists of a nucleotide sequence that encodes the amino acid sequence given in SEQ ID NO:5, or a portion of said protein that comprises at least amino acid residues 158 to 401 of the sequence given in SEQ ID NO:5.

18. An isolated nucleic acid encoding a protein having the amino acid sequence given in SEQ ID NO:5.

19. An isolated nucleic acid consisting of the sequence shown in SEQ ID NO:15, or a portion of said sequence shown in SEQ ID NO:15 of at least 90 consecutive bases.

20. The isolated nucleic acid according to claim 19 wherein said nucleic acid has the sequence shown in SEQ ID NO:15, or portion of said sequence shown in SEQ ID NO:15 of at least 90 consecutive bases.

21. The isolated nucleic acid according to claim 20 wherein the nucleic acid has the sequence shown in SEQ ID NO:15.

* * * * *

```
                             SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
           (A) LENGTH: 17 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 1:

GTTGCAAGAA GAGAAAT                                                  17

(2) INFORMATION FOR SEQ ID NO: 2:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 2:

GAAGATCTGG AGCCCACGGT                                               20
```

(2) INFORMATION FOR SEQ ID NO: 3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

TGATGAAGAT ACCCCACCA                                                      19

(2) INFORMATION FOR SEQ ID NO: 4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

CTGGTCGTTC AAGGTTGGCT GGAGC                                      25

(2) INFORMATION FOR SEQ ID NO: 5:

(i) SEQUENCE CHARACTERISTICS:
        (A) LENGTH: 401 amino acids
        (B) TYPE: amino acid
        (C) STRANDEDNESS:
        (D) TOPOLOGY: linear (ii) MOLECULE TYPE: protein (v) FRAGMENT TYPE: linear (xi) SEQUENCE DESCRIPTION: SEQ ID NO: 5:

```
Met Ser Cys Arg Cys Trp Ile Ser Arg His Pro Ser Tyr Glu Gly Trp
 1               5                  10                  15

Asn Leu Gln Ser Ile Ile Phe His Lys Gln Ile Arg Gly Val Asp Leu
            20                  25                  30

Glu Ser Thr Phe Val Thr Lys Phe Gly Asn Asn Cys Ser Leu Arg Leu
        35                  40                  45

Asn Glu Thr Val Asp Ile His Lys Glu Lys Val Ala Arg Arg Glu Ile
50                  55                  60

Gly Ile Leu Thr Thr Asn Lys Asn Thr Ser Arg Thr His Lys Ile Ile
65                  70                  75                  80

Ala Pro Ala Asn Leu Glu Arg Pro Val Arg Tyr Ile Arg Lys Pro Ile
                85                  90                  95

Asp Tyr Thr Ile Leu Asp Asp Ile Gly His Gly Val Lys Val Ser Thr
            100                 105                 110

Gln Asn Met Lys Met Gly Gly Leu Pro Arg Thr Thr Pro Pro Thr Gln
        115                 120                 125

Lys Pro Pro Ser Pro Pro Met Ser Gly Lys Gly Thr Leu Gly Arg His
    130                 135                 140

Ser Pro Tyr Arg Thr Leu Glu Pro Val Arg Pro Val Val Pro Asn
145                 150                 155                 160

Asp Tyr Val Pro Ser Pro Thr Arg Asn Met Ala Pro Ser Gln Gln Ser
                165                 170                 175

Pro Val Arg Thr Ala Ser Val Asn Gln Arg Asn Arg Thr Tyr Ser Ser
```

```
                    180                 185                 190
Ser Gly Ser Ser Gly Pro Ser His Pro Ser Ser Arg Ser Ser Ser Arg
                195                 200                 205

Glu Asn Ser Gly Ser Gly Ser Val Gly Val Pro Ile Ala Val Pro Thr
    210                 215                 220

Pro Ser Pro Pro Ser Val Phe Pro Gly His Pro Val Gln Phe Tyr Ser
225                 230                 235                 240

Met Asn Arg Pro Ala Ser Arg His Thr Pro Pro Thr Ile Gly Gly Ser
                245                 250                 255

Leu Pro Tyr Arg Arg Pro Pro Ser Ile Thr Ser Gln Thr Ser Leu Gln
                260                 265                 270

Asn Gln Met Asn Gly Gly Pro Phe Tyr Ser Gln Asn Pro Val Ser Asp
            275                 280                 285

Thr Pro Pro Pro Pro Pro Val Glu Glu Pro Val Phe Asp Glu Ser
    290                 295                 300

Pro Pro Pro Pro Pro Pro Glu Asp Tyr Glu Glu Glu Ala Ala
305                 310                 315                 320

Val Val Glu Tyr Ser Asp Pro Tyr Ala Glu Glu Asp Pro Pro Trp Ala
                325                 330                 335

Pro Arg Ser Tyr Leu Glu Lys Val Val Ala Ile Tyr Asp Tyr Thr Lys
            340                 345                 350

Asp Lys Glu Asp Glu Leu Ser Phe Gln Glu Gly Ala Ile Ile Tyr Val
            355                 360                 365

Ile Lys Lys Asn Asp Asp Gly Trp Tyr Glu Gly Val Met Asn Gly Val
            370                 375                 380

Thr Gly Leu Phe Pro Gly Asn Tyr Val Glu Ser Ile Met His Tyr Ser
385                 390                 395                 400

Glu (2) INFORMATION FOR SEQ ID NO: 6:

(i) SEQUENCE CHARACTERISTICS:
        (A) LENGTH: 53 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 6:

Lys Arg Thr Arg Gln Thr Tyr Thr Arg Tyr Gln Thr Leu Glu Leu Glu
1               5                   10                  15

Lys Glu Phe His Phe Asn Arg Tyr Ile Thr Arg Arg Arg Ile Asp
            20                  25                  30

Ile Ala Asn Ala Leu Ser Leu Ser Glu Arg Gln Ile Lys Ile Trp Phe
            35                  40                  45

Gln Asn Arg Arg Met
    50

(2) INFORMATION FOR SEQ ID NO: 7:

(i) SEQUENCE CHARACTERISTICS:
        (A) LENGTH: 53 amino acids
        (B) TYPE: amino acid
        (C) STRANDEDNESS:
        (D) TOPOLOGY: linear (ii) MOLECULE TYPE: protein
```

(xi) SEQUENCE DESCRIPTION: SEQ ID NO: 7:

Lys Arg Gly Arg Thr Ala Tyr Thr Arg Pro Gln Leu Val Glu Leu Glu
1               5                   10                  15

Lys Glu Phe His Phe Asn Arg Tyr Leu Met Arg Pro Arg Arg Val Glu
                20                  25                  30

Met Ala Asn Leu Leu Asn Leu Thr Glu Arg Gln Ile Lys Ile Trp Phe
            35                  40                  45

Gln Asn Arg Arg Met
            50

(2) INFORMATION FOR SEQ ID NO: 8:

(i) SEQUENCE CHARACTERISTICS:
        (A) LENGTH: 53 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 8:

Lys Arg Ser Arg Thr Ala Tyr Thr Arg Gln Gln Val Leu Glu Leu Glu
1               5                   10                  15

Lys Glu Phe His Phe Asn Arg Tyr Leu Thr Arg Arg Arg Ile Glu
                20                  25                  30

Ile Ala His Thr Leu Cys Leu Ser Glu Arg Gln Val Lys Ile Trp Phe
            35                  40                  45

Gln Asn Arg Arg Met
            50

(2) INFORMATION FOR SEQ ID NO: 9:

(i) SEQUENCE CHARACTERISTICS:
        (A) LENGTH: 53 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 9:

Lys Arg Val Arg Thr Ala Tyr Thr Ser Ala Gln Leu Val Glu Leu Glu
1               5                   10                  15

Lys Glu Phe His Phe Asn Arg Tyr Leu Cys Arg Pro Arg Val Glu
                20                  25                  30

Met Ala Asn Leu Leu Asn Leu Thr Glu Arg Gln Ile Lys Ile Trp Phe
            35                  40                  45

Gln Asn Arg Arg Met
            50

(2) INFORMATION FOR SEQ ID NO: 10:

(i) SEQUENCE CHARACTERISTICS:
        (A) LENGTH: 53 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 10:

Lys Arg Ser Arg Thr Ala Tyr Thr Arg Gln Gln Val Leu Glu Leu Glu
1               5                   10                  15

```
Lys Glu Phe His Phe Asn Arg Tyr Leu Thr Arg Arg Arg Ile Glu
            20                  25                  30

Ile Ala His Thr Leu Cys Leu Ser Glu Arg Gln Ile Lys Ile Trp Phe
            35                  40                  45

Gln Asn Arg Arg Met
    50
```

(2) INFORMATION FOR SEQ ID NO: 11:

(i) SEQUENCE CHARACTERISTICS:
        (A) LENGTH: 53 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 11:

```
Lys Arg Gln Arg Thr Ala Tyr Thr Arg Asn Gln Val Leu Glu Leu Glu
1               5                   10                  15

Lys Glu Phe His Thr His Lys Tyr Leu Thr Arg Lys Arg Arg Ile Glu
            20                  25                  30

Val Ala His Ser Leu Met Leu Thr Glu Arg Gln Val Lys Ile Trp Phe
            35                  40                  45

Gln Asn Arg Arg Met
    50
```

(2) INFORMATION FOR SEQ ID NO: 12:

(i) SEQUENCE CHARACTERISTICS:
        (A) LENGTH: 53 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 12:

```
Lys Arg Ser Arg Thr Ala Phe Ser Ser Leu Gln Leu Ile Glu Leu Glu
1               5                   10                  15

Arg Glu Phe His Leu Asn Lys Tyr Leu Ala Arg Thr Arg Arg Ile Glu
            20                  25                  30

Ile Ser Gln Arg Leu Ala Leu Thr Glu Arg Gln Val Lys Ile Trp Phe
            35                  40                  45

Gln Asn Arg Arg Met
    50
```

(2) INFORMATION FOR SEQ ID NO: 13:

(i) SEQUENCE CHARACTERISTICS:
        (A) LENGTH: 47 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 13:

```
Lys Asn Thr Ser Arg Thr His Lys Ile Ile Ala Pro Ala Asn Leu Glu
1               5                   10                  15

Arg Pro Val Arg Tyr Ile Arg Lys Pro Ile Asp Tyr Thr Ile Leu Asp
            20                  25                  30
```

Asp Ile Gly His Gly Val Lys Val Ser Thr Gln Asn Met Lys Met
        35                  40                  45

(2) INFORMATION FOR SEQ ID NO: 14:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 14:

Ile Lys Ile Trp Phe Gln Asn
1               5

(2) INFORMATION FOR SEQ ID NO: 15:

(i) SEQUENCE CHARACTERISTICS:
        (A) LENGTH: 1430 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

```
CCCAATCCTT AGCAAGTGTT GCCTATCTGA TAAACACCTT GGCCAACAAT GTCCTGCAGA      60

TGCTGGATAT CCAGGCATCC CAGCTACGAA GGATGGAATC TTCAATCAAT CATATTTCAC     120

AAGCAAATTA GAGGCGTTGA TCTTGAGTCG ACTTTTGTGA CCAAATTTGG AAACAATTGC     180

AGTTTGAGAT TGAATGAGAC AGTTGATATT CATAAAGAGA AAGTTGCAAG AAGAGAAATT     240

GGTATTTTGA CTACCAATAA AAACACTTCA AGGACACATA AGATTATTGC TCCAGCCAAC     300

CTTGAACGAC CAGTTCGTTA TATTAGAAAA CCTATTGACT ATACAATTCT AGATGATATT     360

GGACATGGAG TAAAGGTGAG TACCCAGAAC ATGAAGATGG GTGGGCTGCC GCGTACAACA     420

CCTCCAACTC AGAAGCCCCC TAGTCCCCCT ATGTCAGGGA AAGGGACACT TGGGCGGCAC     480

TCCCCCTATC GCACACTGGA GCCAGTGCGT CCTCCAGTGG TACCAAATGA TTACGTACCT     540

AGCCCAACCC GTAATATGGC TCCCTCGCAG CAGAGCCCTG TGAGGACAGC TTCTGTGAAT     600

CAAAGAAATC GAACTTACAG CAGCAGTGGG AGTAGTGGAC CCAGCCACCC AAGTAGTCGG     660

AGCAGCAGTC GAGAGAACAG TGGAAGTGGT AGTGTGGGGG TTCCTATTGC TGTTCCTACT     720

CCATCTCCTC CCAGTGTCTT TCCAGGTCAT CCTGTACAGT TCTACAGCAT GAATAGGCCT     780

GCCTCTCGCC ATACTCCCCC AACAATAGGG GGCTCGTTGC CCTATAGACG CCCTCCTTCC     840

ATTACTTCAC AAACAAGCCT TCAGAATCAG ATGAATGGAG GACCTTTTTA TAGCCAGAAT     900

CCAGTTTCAG ATACACCACC TCCACCGCCA CCTGTGGAAG AACCAGTCTT TGATGAGTCT     960

CCCCCACCTC CTCCTCCTCC AGAAGATTAC GAAGAGGAGG AAGCTGCTGT GGTTGAGTAT    1020

AGTGATCCTT ATGCTGAAGA GGACCCACCG TGGGCTCCAC GTTCTTACTT GGAAAAGGTT    1080

GTGGCAATTT ATGACTATAC AAAAGACAAG GAAGATGAGC TGTCCTTTCA GGAAGGAGCC    1140

ATTATTTATG TCATCAAGAA GAATGACGAT GGTTGGTATG AGGGAGTTAT GAATGGAGTG    1200

ACTGGGCTTT TTCCTGGGAA TTACGTTGAG TCTATCATGC ATTATTCTGA GTAAAGCTCA    1260

GCAGGGCTGT GCTTGCCTCA CAGGAATAGT CAGGTCTTCC CAGATTATCT GAAGGCCCTG    1320

GGGATTCCAC TCCAGTAAAG TAGAATGAAG GATACAAATG ATAAAAATTA CACTTTTTTT    1380

TTTGGTTTAT TCCCCAGTAT TAAAAACAAA GCAAGCTGAG TCTGAACAAA               1430
```

(2) INFORMATION FOR SEQ ID NO: 16:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: protein (v) FRAGMENT TYPE: linear (xi) SEQUENCE DESCRIPTION: SEQ ID NO: 16:

Pro Xaa Xaa Pro